(12) United States Patent
Gros et al.

(10) Patent No.: US 10,301,386 B2
(45) Date of Patent: May 28, 2019

(54) ANTIBODY THERAPEUTICS THAT BIND CD147

(71) Applicant: Sorrento Therapeutics, Inc., San Diego, CA (US)

(72) Inventors: Edwige Gros, San Diego, CA (US); Heyue Zhou, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 38 days.

(21) Appl. No.: 15/304,358

(22) PCT Filed: Apr. 14, 2015

(86) PCT No.: PCT/US2015/025824
§ 371 (c)(1),
(2) Date: Oct. 14, 2016

(87) PCT Pub. No.: WO2015/160853
PCT Pub. Date: Oct. 22, 2015

(65) Prior Publication Data
US 2017/0037129 A1  Feb. 9, 2017

Related U.S. Application Data

(60) Provisional application No. 61/980,544, filed on Apr. 16, 2014.

(51) Int. Cl.
*C07K 16/28* (2006.01)
*C07K 16/30* (2006.01)

(52) U.S. Cl.
CPC ...... *C07K 16/2803* (2013.01); *C07K 16/3015* (2013.01); *C07K 16/3023* (2013.01); *C07K 16/3046* (2013.01); *C07K 16/3069* (2013.01); *C07K 2317/21* (2013.01); *C07K 2317/33* (2013.01); *C07K 2317/55* (2013.01); *C07K 2317/565* (2013.01); *C07K 2317/622* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| 2005/0180977 | A1 | 8/2005 | Nixon et al. | |
|---|---|---|---|---|
| 2007/0237776 | A1 | 10/2007 | Huang et al. | |
| 2011/0200627 | A1* | 8/2011 | Cunningham | C07K 16/2803 424/185.1 |

FOREIGN PATENT DOCUMENTS

WO  94/45031 A2  9/1999

OTHER PUBLICATIONS

McCarthy et al. (J. Innnnunol. Methods, 251(1-2): 137-149, 2001).*
Lin et al. (African Journal of Biotechnology, 10(79):18294-18302, 2011).*
Mariuzza (Annu. Rev. Biophys. Biophys. Chem., 16: 139-159, 1987).*
Griffiths, A.D. et al., "Human anti-self antibodies with high specificity from phage," Embo J. 12 (2), 725-734 (1993).
Written Opinion of the International Searching Authority and International Search Report relating to International Application No. PCT/US 2015/25824, dated Sep. 23, 2015 and mailed on Oct. 16, 2015.
Lijuan Xiong et al: "The Biological Function and Clincal Utilization of CD147 in Human Diseases: A Review of the Current Scientific Literature," International Journal of Molecular Sciences, vol. 15, No. 10, Sep. 29, 2014 (Sep. 29, 2014), pp. 17411-17441, SP055374401, DOI: 10.3390/ijms151017411.
Larissa Sweeny et al: "A novel extracellular drug conjugate significantly inhibits head and neck squamous cell carcinoma", Oral Oncology, vol. 49, No. 10, Oct. 1, 2013 (Oct. 1, 2013), pp. 991-997, XP055152770, ISSN: 1368-8375, DOI: 10.1016/j.oraloncology.2013.07.006.
Zhao Shuang et al: "CD147 promotes MTX resistance by immune cells through up-regulating ABCG2 expression and function", Journal of Dermatological Science, Elsevier, Amsterdam, NL, vol. 70, No. 3, Feb. 28, 2013 (Feb. 28, 2013), pp. 182-189, XP028543638, ISSN: 0923-1811, DOI: 10.1016/J.JDERMSCI.2013.02.005.

(Continued)

*Primary Examiner* — Nelson B Moseley, II
(74) *Attorney, Agent, or Firm* — Womble Bond Dickinson (US) LLP; Danielle L. Herritt; Cristin H. Cowles

(57) ABSTRACT

There is disclosed compositions and methods relating to or derived from anti-CD147 antibodies. More specifically, there is disclosed fully human antibodies that bind CD147, CD147-binding fragments and derivatives of such antibodies, and CD147-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having CD147 related disorders or conditions. There is also disclosed a method for treating CD147-expressing tumors, including hepatocellular carcinomas and squamous carcinomas, and non-oncology diseases selected from the group consisting of rheumatoid arthritis, experimental lung injury, atherosclerosis, chronic liver disease induced by hepatitis C virus, ischemic myocardial injury and heart failure.

15 Claims, 5 Drawing Sheets

Specification includes a Sequence Listing.

(56) References Cited

OTHER PUBLICATIONS

Supplemental European Search Report Regarding EP Application No. 15 780 333.9, dated Jun. 14, 2017 and issued on Oct. 10, 2017.
Supplementary Partial European Search Report related to Application No. 15780333.9, dated Jun. 14, 2017 and issued on Jul. 4, 2017.
International Preliminary Report on Patentability relating to International Application No. PCT/2015/025824, dated Oct. 18, 2016.

* cited by examiner

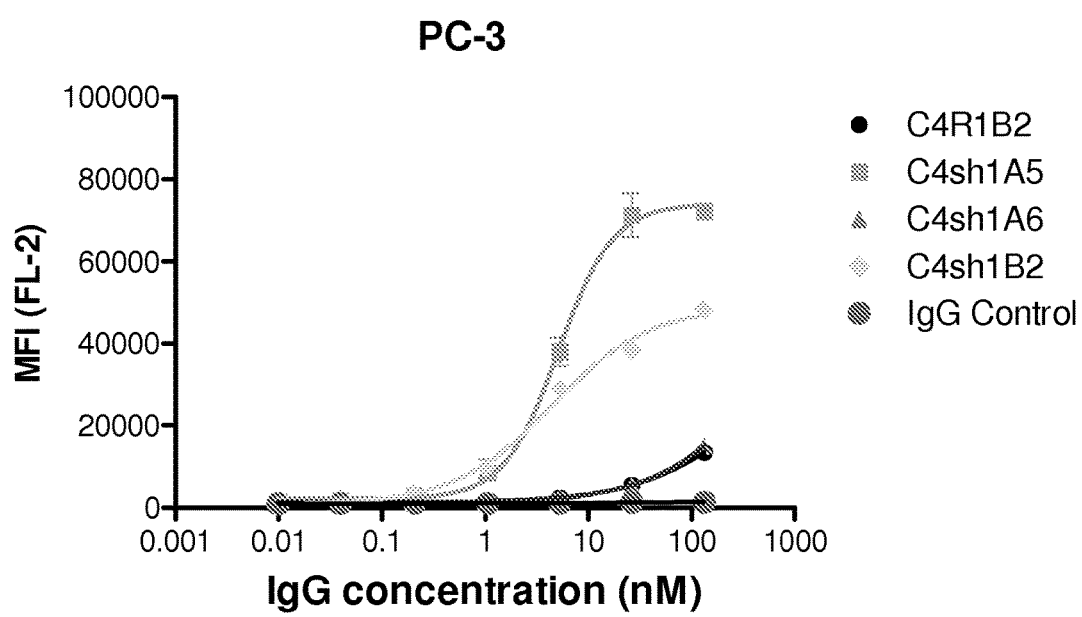
Figure 3-A

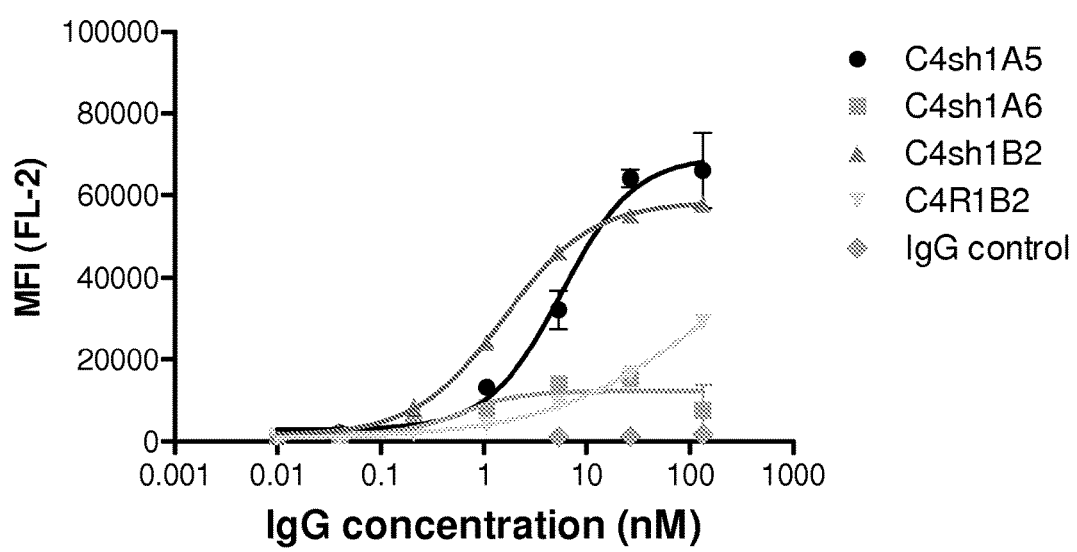
Figure 3-B

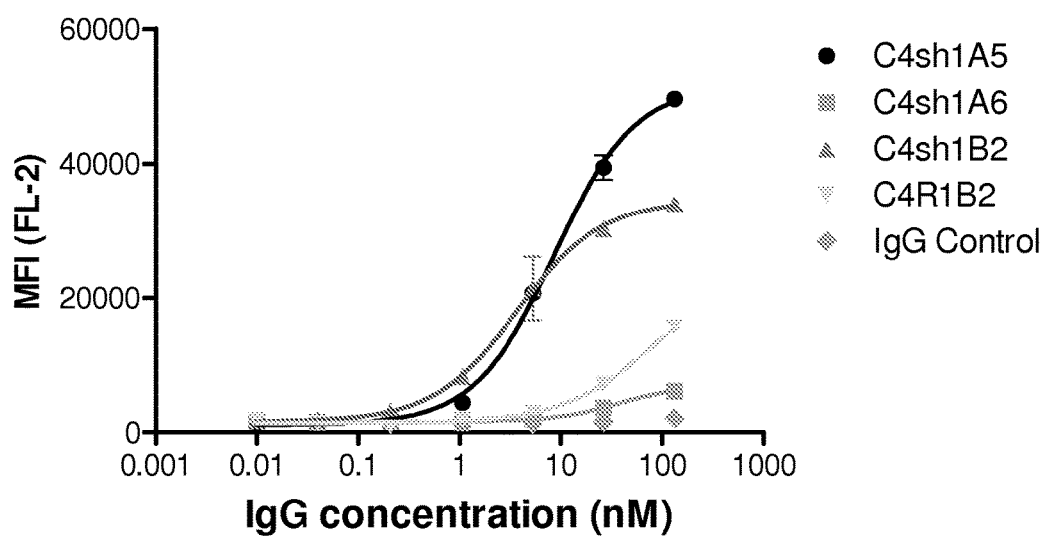
Figure 3-C

ANTIBODY THERAPEUTICS THAT BIND CD147

REFERENCE TO RELATED APPLICATIONS

This application is a U.S. National Stage application under 35 U.S.C. 371 of International Application No. PCT/US2015/025824, filed on Apr. 14, 2015, which claims priority to U.S. Provisional Application No. 61/980,544, filed Apr. 16, 2014. The entire contents of each of the aforementioned applications are incorporated herein by reference.

SEQUENCE LISTING

The instant application contains a Sequence Listing which has been submitted electronically and is hereby incorporated by reference in its entirety. Said document is named S103014 1280US-PCT0245-9 SL.txt and is 64 kilobytes in size.

TECHNICAL FIELD

The present disclosure provides compositions and methods relating to or derived from anti-CD147 antibodies. More specifically, the present disclosure provides fully human antibodies that bind CD147, CD147-binding fragments and derivatives of such antibodies, and CD147-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having CD147 related disorders or conditions. The present disclosure further provides a method for treating CD147-expressing tumors, including hepatocellular carcinomas and squamous carcinomas, and non-oncology diseases selected from the group consisting of rheumatoid arthritis, experimental lung injury, atherosclerosis, chronic liver disease induced by hepatitis C virus, ischemic myocardial injury and heart failure.

BACKGROUND

CD147 is involved in many physiological functions, such as lymphocyte responsiveness, spermatogenesis, implantation, fertilization and neurological functions at early stages of development. CD147 is a member of the immunoglobulin family of receptors. Members of this family play a role in intercellular communication involved in many immune-related functions, differentiation and development. CD147 plays a role in spermatogenesis, lymphocyte activation, expression of monocarboxylate transporters (MCT) and has been identified as a regulatory subunit of the γ-secretase complex in Alzheimer's disease amyloid β-peptide production (Gabison and Mourah Connect Tissue Res. 49:175-179, 2008; Iacono et al. Exp. Mol. Pathol. 83:283-295, 2007; Nabeshima et al. Pathol. Int. 56:359-367, 2006; Gabison et al. Biochimie 87:361-368, 2005; and Muramatsu et al. Histol. Histopathol. 18: 981-987, 2003).

Some of these insights were obtained from the study of cd147−/− mice. These animals are defective in matrix metalloproteinase (MMP) regulation, spermatogenesis, lymphocyte responsiveness and neurological functions at the early stages of development. Such female mice are infertile due to failure of implantation and fertilization (Muramatsu et al. Histol. Histopathol. 18: 981-987, 2003). CD147 is involved in the transport of the MCT-1 and MCT-3 to the plasma membrane since reduced accumulation of these transporters has been observed in the retina of cd147 knockout mice. A functional role of CD147 in cell adhesion is supported by its involvement in the blood-brain barrier and its interactions with integrins.

CD147 has been implicated in many pathological processes, such as rheumatoid arthritis, experimental lung injury, atherosclerosis, chronic liver disease induced by hepatitis C virus, ischemic myocardial injury and heart failure (Gabison et al. Biochimie 87:361-368, 2005). Treatment of transplant patients with a CD147 antibody was effective due to inhibition of T-cell activation (Deeg et al., Blood 98:2052-2058, 2001).

CD147, a transmembrane protein of the immunoglobulin (Ig) superfamily was identified independently in different species and has many designations across different species such as M6, Neurothelin, 5A11, HT7, OX-47, CE9, EMMPRIN, Basigin, and gp42 (Kasinrerk et al. J. Immunol. 149:847-854, 1992; Altruda et al. Gene 85:445-451, 1989; Miyauchi et al. J. Biochem. 107:316-323, 1990; Seulberger et al. EMBO J. 9:2151-2158, 1990; and Fossum et al. Eur. J. Immunol. 21:671-679, 1991). The most prevalent standard isoform is a single-chain type I transmembrane molecule composed of a 21 amino acid signal sequence, a 186 residues-long extracellular domain consisting of two Ig-like domains, a transmembrane domain of 21 amino acids and a cytoplasmic domain of 41 residues.

The transmembrane region harbors a leucine zipper and a charged residue (glutamic acid). The corresponding gene is located on chromosome 19p13.3 and encodes a 29 kDa backbone protein. Three N glycosylation sites have been identified and migration on sodium dodecyl-sulfate polyacrylamide gel electrophoresis (SDS-PAGE) occurs between 39 and 65 kDa depending on the degree of glycosylation.

CD147 has a broad expression pattern on hematopoietic and non-hematopoietic cells such as monocytes, granulocytes, epithelial and endothelial cells. Weak expression has been noted on resting T lymphocytes, whereas expression is increased on activated T lymphocytes and monocytes (Kasinrerk et al. J. Immunol. 149:847-854, 1992; Altruda et al. Gene 85:445-451, 1989; Miyauchi et al. J. Biochem. 107:316-323, 1990; Seulberger et al. EMBO J. 9:2151-2158, 1990; Fossum et al. Eur. J. Immunol. 21:671-679, 1991; and Ochrietor et al. Invest. Ophthalmol. Vis. Sci. 44:4086-4096, 2003). The perfect conservation of the amino acid sequences of the transmembrane sequences across all listed species (Iacono et al. Exp. Mol. Pathol. 83:283-295, 2007) as described above is a remarkable feature, which includes the presence of a conserved glutamic acid residue. This finding indicates the involvement of transmembrane amino acids in protein-protein interactions within the plasma membrane. The cytoplasmic domains are more conserved than the extracellular domains pointing to similar considerations with respect to conserved protein-protein interactions with proteins located in the cytoplasm. Inhibition of CD147 expression by RNAi led to significantly decreased angiogenesis in vitro. CD147 may regulate angiogenesis by several mechanisms including proliferation, survival, MMP secretion and phosphoinositide 3 kinase/protein kinase B (PI3K/Akt) activation.

In several cancer cell lines, CD147 has been identified as a mediator of anti-apoptotic function and chemoresistance. In HO-8910 ovarian carcinoma cells, CD147 RNAi reduces tumor cell invasion, tumorigenicity and chemosensitivity to paclitaxel (Zou et al. *Cancer Lett.* 248: 211-218, 2007). Up-regulation of CD147 has been observed in several multidrug-resistant cancer cell lines (Toole et al. *Drug Resist. Update* 11:110-121, 2008).

Independently, involvement of CD147 in resistance of cancer cells to a variety of chemotherapeutic agents was reported (Li et al. *Cell. Mol. Life Sci.* 66:504-515, 2009). In addition, CD147 was identified as a receptor which promotes androgen-independent growth of tumor cells in a hyaluronan-dependent manner (Marieb et al. *Cancer Res.* 64:1229-1232, 2004). In human oral squamous carcinoma cells (SCC), CD147-directed RNAi reduced X-chromosome linked inhibitor of apoptosis protein (XIAP) expression and increased chemosensitivity to 5 fluorouracil (Kuang et al. *Cancer Lett.* 276:189-195, 2009). In breast cancer cell lines, it was shown that CD147 confers resistance to anoikis as demonstrated by activation of caspase.

Many mAbs directed against CD147 interacting with distinct epitopes have been established (Koch et al. *Int. Immunol.* 11:777-786, 1999). Most of the antibodies only bind to phytohemagglutinin (PHA) stimulated T-cells, not to resting T-cells. This phenomenon was explained by bivalent binding of the low-affinity antibodies to clustered CD147 molecules on activated T-cells and not by neoepitopes specifically displayed on activated T-cells. High affinity antibodies were able to bind in a monovalent fashion to resting T-cells, which are low expressors of CD147.

Induction of dimerisation by the low-affinity antibodies resulted in inhibition of CD3-mediated T-cell activation. High-affinity mAb MEM-M6/6, recognizing a unique epitope, inhibits T cell activation by 80% and as outlined in a previous section also proliferation of colon cancer and melanoma cells and not non-transformed fibroblasts (Baba et al. *Biochem. Biophys. Res. Commun.* 374:111-116, 2008). Triggering of CD147 by mAbs was shown to cause displacement of glycosylphosphatidylinositol (GPI)-anchored co-receptors CD48 and CD59 from microdomains in human T-lymphocytes (Staffler et al. *J. Immunol.* 171:1707-1714, 2003). Perturbation of microdomains is responsible for inhibition of T-cell proliferation. Making use of COS-7 transfectants and mAbs covering different CD147 epitopes, it was shown that CD147 contains different epitopes involved in regulation of cell adhesion (homotypic cell aggregation) and lymphocyte activation (Chiampanichayakul et al. *Immunobiology* 211:167-78, 2006).

A different set of CD147-directed mAbs were evaluated with respect to treatment of hepatocellular carcinoma (HCC) (Xu et al. *Mol. Cancer Res.* 5:605-614, 2007). mAb Hb18G and Licartin, a 131I-labeled F(ab')2 fragment of mAb Hb18G) mediate suppression of MMP secretion in cocultured fibroblasts and inhibit invasion, and Licartin significantly inhibited the growth of HCC cells. mAb Hb18G and Licartin effectively reduced growth and metastasis as well as the expression of stromal factors such as MMPs, VEGF and fibroblast surface protein (Xu et al. *Mol. Cancer Res.* 5:605-614, 2007). Clinical studies were reported for targeted radioimmunotherapy of HCC patients with Licartin (Xu et al. *Hepatology* 45:269-276, 2007). Of the 73 patients completing two cycles in a phase II trial, 6 (8%) were noted to have a partial response, 14 (19%) a minor response and 43 (59%) had stable disease. The survival of progression-free patients was significantly higher than that of patients with progressive disease. Chimeric CD147 antibody (IgG1) referred to as CNTO 3899 was evaluated as an agent for potential treatment of head-and-neck squamous cell carcinoma (Dean et al. *Clin. Cancer Res.* 15:4058-4065, 2009). The antibody inhibited proliferation of SSC-1 and FaDu cells up to 57%. Inhibition of collagen degradation was noted as well. Significant tumor growth inhibition was noted in SSC-1 xenografts. CNTO 3899 augments radiation response of SSC-1 and FaDu cells in vitro and in xenografts. Furthermore, the same study showed that CD147 function is associated with cytokine production of proinflammatory and proangiogenic factors such as IL1β, IL6, IL8 and VEGF. Inhibition of cytokines, MMPs and VEGF seems to mediate the mechanism of action of this mAb. The studies as outlined would suggest that inhibition of proliferation of tumor cells by CD147 mAbs in the absence of immune effector cells is either cell-type-specific and/or might be dependent on distinct epitopes the mAbs are directed against. Inhibition of T-cell activation and/or depletion was not investigated with CNTO 3899, Hb18G or Licartin.

SUMMARY

The present disclosure provides a fully human antibody of an IgG class that binds to a CD147 epitope with a binding affinity of at least $10^{-6}$ M, which has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 26, SEQ ID NO. 28, SEQ ID NO. 30, SEQ ID NO. 34, SEQ ID NO. 36, SEQ ID NO. 38, SEQ ID NO. 41, SEQ ID NO. 43, SEQ ID NO. 46, SEQ ID NO. 48, SEQ ID NO. 50, SEQ ID NO. 53, SEQ ID NO. 56, SEQ ID NO. 59, SEQ ID NO. 62, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 35, SEQ ID NO. 37, SEQ ID NO. 39, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 52, SEQ ID NO. 54, SEQ ID NO. 55, SEQ ID NO. 57, SEQ ID NO. 58, SEQ ID NO. 60, SEQ ID NO. 61, SEQ ID NO. 63, and combinations thereof. Preferably, the fully human antibody has both a heavy chain and a light chain wherein the antibody has a heavy chain/light chain variable domain sequence selected from the group consisting SEQ ID NO. 1/SEQ ID NO. 2 (called C4R1A2 herein), SEQ ID NO. 3/SEQ ID NO. 4 (called C4R1A5 herein), SEQ ID NO. 5/SEQ ID NO. 6 (called C4R1A6 herein), SEQ ID NO. 7/SEQ ID NO. 8 (called C4R1A8 herein), SEQ ID NO. 9/SEQ ID NO. 10 (called C4R1A9 herein), SEQ ID NO. 11/SEQ ID NO. 12 (called C4R1B2 herein), SEQ ID NO. 13/SEQ ID NO. 14 (called C4R1C10 herein), SEQ ID NO. 15/SEQ ID NO. 16 (called C4R1C11 herein), SEQ ID NO. 17/SEQ ID NO. 18 (called C4R1C3 herein), SEQ ID NO. 19/SEQ ID NO. 20 (called C4R1D11 herein), SEQ ID NO. 21/SEQ ID NO. 22 (called C4R1F12 herein), SEQ ID NO. 13/SEQ ID NO. 25 (called C4R1G1 herein), SEQ ID NO. 26/SEQ ID NO. 27 (called C4R1G4 herein), SEQ ID NO. 28/SEQ ID NO. 29 (called C4R1G7 herein), SEQ ID NO. 30/SEQ ID NO. 31 (called C4R1H10 herein), SEQ ID NO. 13/SEQ ID NO. 32 (called C4R1H11 herein), SEQ ID NO. 13/SEQ ID NO. 33 (called C4R1H4 herein), SEQ ID NO. 34/SEQ ID NO. 35 (called C4sh1A1 herein), SEQ ID NO. 36/SEQ ID NO. 37 (called C4sh1A2 herein), SEQ ID NO.

38/SEQ ID NO. 39 (called C4sh1A3 herein), SEQ ID NO. 38/SEQ ID NO. 40 (called C4sh1A4 herein), SEQ ID NO. 41/SEQ ID NO. 42 (called C4sh1A5 herein), SEQ ID NO. 43/SEQ ID NO. 44 (called C4sh1A6 herein), SEQ ID NO. 38/SEQ ID NO. 45 (called C4sh1A9 herein), SEQ ID NO. 46/SEQ ID NO. 47 (called C4sh1B10 herein), SEQ ID NO. 48/SEQ ID NO. 49 (called C4sh1B11 herein), SEQ ID NO. 50/SEQ ID NO. 51 (called C4sh1B2 herein), SEQ ID NO. 38/SEQ ID NO. 52 (called C4sh1C10 herein), SEQ ID NO. 53/SEQ ID NO. 54 (called C4sh1C5 herein), SEQ ID NO. 41/SEQ ID NO. 54 (called C4sh1C6 herein), SEQ ID NO. 56/SEQ ID NO. 57 (called C4sh1E10 herein), SEQ ID NO. 38/SEQ ID NO. 58 (called C4sh1E12 herein), SEQ ID NO. 59/SEQ ID NO. 60 (called C4sh1F11 herein), SEQ ID NO. 38/SEQ ID NO. 61 (called C4sh1G4 herein), SEQ ID NO. 62/SEQ ID NO. 63 (called C4sh1H9 herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 26, SEQ ID NO. 28, SEQ ID NO. 30, SEQ ID NO. 34, SEQ ID NO. 36, SEQ ID NO. 38, SEQ ID NO. 41, SEQ ID NO. 43, SEQ ID NO. 46, SEQ ID NO. 48, SEQ ID NO. 50, SEQ ID NO. 53, SEQ ID NO. 56, SEQ ID NO. 59, SEQ ID NO. 62, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 35, SEQ ID NO. 37, SEQ ID NO. 39, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 52, SEQ ID NO. 54, SEQ ID NO. 55, SEQ ID NO. 57, SEQ ID NO. 58, SEQ ID NO. 60, SEQ ID NO. 61, SEQ ID NO. 63, and combinations thereof. Preferably, the fully human antibody Fab fragment has both a heavy chain variable domain region and a light chain variable domain region wherein the antibody has a heavy chain/light chain variable domain sequence selected from the group consisting SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 13/SEQ ID NO. 25, SEQ ID NO. 26/SEQ ID NO. 27, SEQ ID NO. 28/SEQ ID NO. 29, SEQ ID NO. 30/SEQ ID NO. 31, SEQ ID NO. 13/SEQ ID NO. 32, SEQ ID NO. 13/SEQ ID NO. 33, SEQ ID NO. 34/SEQ ID NO. 35, SEQ ID NO. 36/SEQ ID NO. 37, SEQ ID NO. 38/SEQ ID NO. 39, SEQ ID NO. 38/SEQ ID NO. 40, SEQ ID NO. 41/SEQ ID NO. 42, SEQ ID NO. 43/SEQ ID NO. 44, SEQ ID NO. 38/SEQ ID NO. 45, SEQ ID NO. 46/SEQ ID NO. 47, SEQ ID NO. 48/SEQ ID NO. 49, SEQ ID NO. 50/SEQ ID NO. 51, SEQ ID NO. 38/SEQ ID NO. 52, SEQ ID NO. 53/SEQ ID NO. 54, SEQ ID NO. 41/SEQ ID NO. 54, SEQ ID NO. 56/SEQ ID NO. 57, SEQ ID NO. 38/SEQ ID NO. 58, SEQ ID NO. 59/SEQ ID NO. 60, SEQ ID NO. 38/SEQ ID NO. 61, SEQ ID NO. 62/SEQ ID NO. 63, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 26, SEQ ID NO. 28, SEQ ID NO. 30, SEQ ID NO. 34, SEQ ID NO. 36, SEQ ID NO. 38, SEQ ID NO. 41, SEQ ID NO. 43, SEQ ID NO. 46, SEQ ID NO. 48, SEQ ID NO. 50, SEQ ID NO. 53, SEQ ID NO. 56, SEQ ID NO. 59, SEQ ID NO. 62, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 35, SEQ ID NO. 37, SEQ ID NO. 39, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 52, SEQ ID NO. 54, SEQ ID NO. 55, SEQ ID NO. 57, SEQ ID NO. 58, SEQ ID NO. 60, SEQ ID NO. 61, SEQ ID NO. 63, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 13/SEQ ID NO. 25, SEQ ID NO. 26/SEQ ID NO. 27, SEQ ID NO. 28/SEQ ID NO. 29, SEQ ID NO. 30/SEQ ID NO. 31, SEQ ID NO. 13/SEQ ID NO. 32, SEQ ID NO. 13/SEQ ID NO. 33, SEQ ID NO. 34/SEQ ID NO. 35, SEQ ID NO. 36/SEQ ID NO. 37, SEQ ID NO. 38/SEQ ID NO. 39, SEQ ID NO. 38/SEQ ID NO. 40, SEQ ID NO. 41/SEQ ID NO. 42, SEQ ID NO. 43/SEQ ID NO. 44, SEQ ID NO. 38/SEQ ID NO. 45, SEQ ID NO. 46/SEQ ID NO. 47, SEQ ID NO. 48/SEQ ID NO. 49, SEQ ID NO. 50/SEQ ID NO. 51, SEQ ID NO. 38/SEQ ID NO. 52, SEQ ID NO. 53/SEQ ID NO. 54, SEQ ID NO. 41/SEQ ID NO. 54, SEQ ID NO. 56/SEQ ID NO. 57, SEQ ID NO. 38/SEQ ID NO. 58, SEQ ID NO. 59/SEQ ID NO. 60, SEQ ID NO. 38/SEQ ID NO. 61, SEQ ID NO. 62/SEQ ID NO. 63, and combinations thereof.

The present disclosure further provides a method for treating rheumatoid arthritis, experimental lung injury, atherosclerosis, chronic liver disease induced by hepatitis C virus, ischemic myocardial injury and heart failure, comprising administering an anti-CD147 polypeptide, wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 26, SEQ ID NO. 28, SEQ ID NO.

30, SEQ ID NO. 34, SEQ ID NO. 36, SEQ ID NO. 38, SEQ ID NO. 41, SEQ ID NO. 43, SEQ ID NO. 46, SEQ ID NO. 48, SEQ ID NO. 50, SEQ ID NO. 53, SEQ ID NO. 56, SEQ ID NO. 59, SEQ ID NO. 62, and combinations thereof, and that has a light chain variable domain sequence that is at least 95% identical to the amino acid consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 35, SEQ ID NO. 37, SEQ ID NO. 39, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 52, SEQ ID NO. 54, SEQ ID NO. 55, SEQ ID NO. 57, SEQ ID NO. 58, SEQ ID NO. 60, SEQ ID NO. 61, SEQ ID NO. 63, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 26, SEQ ID NO. 28, SEQ ID NO. 30, SEQ ID NO. 34, SEQ ID NO. 36, SEQ ID NO. 38, SEQ ID NO. 41, SEQ ID NO. 43, SEQ ID NO. 46, SEQ ID NO. 48, SEQ ID NO. 50, SEQ ID NO. 53, SEQ ID NO. 56, SEQ ID NO. 59, SEQ ID NO. 62, and combinations thereof, and that has the light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 35, SEQ ID NO. 37, SEQ ID NO. 39, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 52, SEQ ID NO. 54, SEQ ID NO. 55, SEQ ID NO. 57, SEQ ID NO. 58, SEQ ID NO. 60, SEQ ID NO. 61, SEQ ID NO. 63, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 26, SEQ ID NO. 28, SEQ ID NO. 30, SEQ ID NO. 34, SEQ ID NO. 36, SEQ ID NO. 38, SEQ ID NO. 41, SEQ ID NO. 43, SEQ ID NO. 46, SEQ ID NO. 48, SEQ ID NO. 50, SEQ ID NO. 53, SEQ ID NO. 56, SEQ ID NO. 59, SEQ ID NO. 62, and combinations thereof, and that has the light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 35, SEQ ID NO. 37, SEQ ID NO. 39, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 52, SEQ ID NO. 54, SEQ ID NO. 55, SEQ ID NO. 57, SEQ ID NO. 58, SEQ ID NO. 60, SEQ ID NO. 61, SEQ ID NO. 63, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2 (called C4R1A2 herein), SEQ ID NO. 3/SEQ ID NO. 4 (called C4R1A5 herein), SEQ ID NO. 5/SEQ ID NO. 6 (called C4R1A6 herein), SEQ ID NO. 7/SEQ ID NO. 8 (called C4R1A8 herein), SEQ ID NO. 9/SEQ ID NO. 10 (called C4R1A9 herein), SEQ ID NO. 11/SEQ ID NO. 12 (called C4R1B2 herein), SEQ ID NO. 13/SEQ ID NO. 14 (called C4R1C10 herein), SEQ ID NO. 15/SEQ ID NO. 16 (called C4R1C11 herein), SEQ ID NO. 17/SEQ ID NO. 18 (called C4R1C3 herein), SEQ ID NO. 19/SEQ ID NO. 20 (called C4R1D11 herein), SEQ ID NO. 21/SEQ ID NO. 22 (called C4R1F12 herein), SEQ ID NO. 13/SEQ ID NO. 25 (called C4R1G1 herein), SEQ ID NO. 26/SEQ ID NO. 27 (called C4R1G4 herein), SEQ ID NO. 28/SEQ ID NO. 29 (called C4R1G7 herein), SEQ ID NO. 30/SEQ ID NO. 31 (called C4RH10 herein), SEQ ID NO. 13/SEQ ID NO. 32 (called C4R1H11 herein), SEQ ID NO. 13/SEQ ID NO. 33 (called C4R1H4 herein), SEQ ID NO. 34/SEQ ID NO. 35 (called C4sh1A1 herein), SEQ ID NO. 36/SEQ ID NO. 37 (called C4sh1A2 herein), SEQ ID NO. 38/SEQ ID NO. 39 (called C4sh1A3 herein), SEQ ID NO. 38/SEQ ID NO. 40 (called C4sh1A4 herein), SEQ ID NO. 41/SEQ ID NO. 42 (called C4sh1A5 herein), SEQ ID NO. 43/SEQ ID NO. 44 (called C4sh1A6 herein), SEQ ID NO. 38/SEQ ID NO. 45 (called C4sh1A9 herein), SEQ ID NO. 46/SEQ ID NO. 47 (called C4sh1B10 herein), SEQ ID NO. 48/SEQ ID NO. 49 (called C4sh1B11 herein), SEQ ID NO. 50/SEQ ID NO. 51 (called C4sh1B2 herein), SEQ ID NO. 38/SEQ ID NO. 52 (called C4sh1C10 herein), SEQ ID NO. 53/SEQ ID NO. 54 (called C4sh1C5 herein), SEQ ID NO. 41/SEQ ID NO. 54 (called C4sh1C6 herein), SEQ ID NO. 56/SEQ ID NO. 57 (called C4sh1E10 herein), SEQ ID NO. 38/SEQ ID NO. 58 (called C4sh1E12 herein), SEQ ID NO. 59/SEQ ID NO. 60 (called C4sh1F11 herein), SEQ ID NO. 38/SEQ ID NO. 61 (called C4sh1G4 herein), SEQ ID NO. 62/SEQ ID NO. 63 (called C4sh1H9 herein), and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called C4R1A2 herein), SEQ ID NO. 3/SEQ ID NO. 4 (called C4R1A5 herein), SEQ ID NO. 5/SEQ ID NO. 6 (called C4R1A6 herein), SEQ ID NO. 7/SEQ ID NO. 8 (called C4R1A8 herein), SEQ ID NO. 9/SEQ ID NO. 10 (called C4R1A9 herein), SEQ ID NO. 11/SEQ ID NO. 12 (called C4R1B2 herein), SEQ ID NO. 13/SEQ ID NO. 14 (called C4R1C10 herein), SEQ ID NO. 15/SEQ ID NO. 16 (called C4R1C11 herein), SEQ ID NO. 17/SEQ ID NO. 18 (called C4R1C3 herein), SEQ ID NO. 19/SEQ ID NO. 20 (called C4R1D11 herein), SEQ ID NO. 21/SEQ ID NO. 22 (called C4R1F12 herein), SEQ ID NO. 13/SEQ ID NO. 25 (called C4R1G1 herein), SEQ ID NO. 26/SEQ ID NO. 27 (called C4R1G4 herein), SEQ ID NO. 28/SEQ ID NO. 29 (called C4R1G7 herein), SEQ ID NO. 30/SEQ ID NO. 31 (called C4RH10 herein), SEQ ID NO. 13/SEQ ID NO. 32 (called C4R1H11 herein), SEQ ID NO. 13/SEQ ID NO. 33 (called C4R1H4 herein), SEQ ID NO. 34/SEQ ID NO. 35 (called C4sh1A1 herein), SEQ ID NO. 36/SEQ ID NO. 37 (called C4sh1A2 herein), SEQ ID NO. 38/SEQ ID NO. 39 (called C4sh1A3 herein), SEQ ID NO. 38/SEQ ID NO. 40 (called C4sh1A4 herein), SEQ ID NO. 41/SEQ ID NO. 42 (called C4sh1A5 herein), SEQ ID NO. 43/SEQ ID NO. 44 (called C4sh1A6 herein), SEQ ID NO. 38/SEQ ID NO. 45 (called C4sh1A9 herein), SEQ ID NO. 46/SEQ ID NO. 47 (called C4sh1B10 herein), SEQ ID NO. 48/SEQ ID NO. 49 (called C4sh1B11 herein), SEQ ID NO. 50/SEQ ID NO. 51 (called C4sh1B2 herein), SEQ ID NO. 38/SEQ ID NO. 52 (called C4sh1C10 herein), SEQ ID NO. 53/SEQ ID NO. 54 (called C4sh1C5 herein), SEQ ID NO. 41/SEQ ID NO. 54 (called C4sh1C6 herein), SEQ ID NO. 56/SEQ ID NO. 57 (called C4sh1E10 herein), SEQ ID NO. 38/SEQ ID NO. 58 (called C4sh1E12 herein), SEQ ID NO. 59/SEQ ID NO. 60 (called C4sh1F11 herein), SEQ ID NO. 38/SEQ ID NO. 61 (called C4sh1G4 herein), SEQ ID NO. 62/SEQ ID NO. 63 (called C4sh1H9 herein), and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 13/SEQ ID NO. 25, SEQ ID NO. 26/SEQ ID NO. 27, SEQ ID NO. 28/SEQ ID NO. 29, SEQ ID NO. 30/SEQ ID NO. 31, SEQ ID NO. 13/SEQ ID NO. 32, SEQ ID NO. 13/SEQ ID NO. 33, SEQ ID NO. 34/SEQ ID NO. 35, SEQ ID NO. 36/SEQ ID NO. 37, SEQ ID NO. 38/SEQ ID NO. 39, SEQ ID NO. 38/SEQ ID NO. 40, SEQ ID NO. 41/SEQ ID NO. 42, SEQ ID NO. 43/SEQ ID NO. 44, SEQ ID NO. 38/SEQ ID NO. 45, SEQ ID NO. 46/SEQ ID NO. 47, SEQ ID NO. 48/SEQ ID NO. 49, SEQ ID NO. 50/SEQ ID NO. 51, SEQ ID NO. 38/SEQ ID NO. 52, SEQ ID NO. 53/SEQ ID NO. 54, SEQ ID NO. 41/SEQ ID NO. 54, SEQ ID NO. 56/SEQ ID NO. 57, SEQ ID NO. 38/SEQ ID NO. 58, SEQ ID NO. 59/SEQ ID NO. 60, SEQ ID NO. 38/SEQ ID NO. 61, SEQ ID NO. 62/SEQ ID NO. 63, and combinations thereof.

Preferably, the method is for treating various cancers, rheumatoid arthritis, experimental lung injury, atherosclerosis, chronic liver disease induced by hepatitis C virus, ischemic myocardial injury and heart failure.

DESCRIPTION OF THE DRAWINGS

FIG. 3-A shows the binding of exemplary anti-CD147 antibodies to Human CD147 expressed at the surface of prostate cancer cells (PC3), as analyzed by flow cytometry.

FIG. 3-B shows the binding of exemplary anti-CD147 antibodies to Human CD147 expressed at the surface of myeloid leukemia cells (K562), as analyzed by flow cytometry.

FIG. 3-C shows the binding of exemplary anti-CD147 antibodies to Human CD147 expressed at the surface of Non-Small Cell Lung Carcinoma cells (A549), as analyzed by flow cytometry.

DETAILED DESCRIPTION

Figure 1:
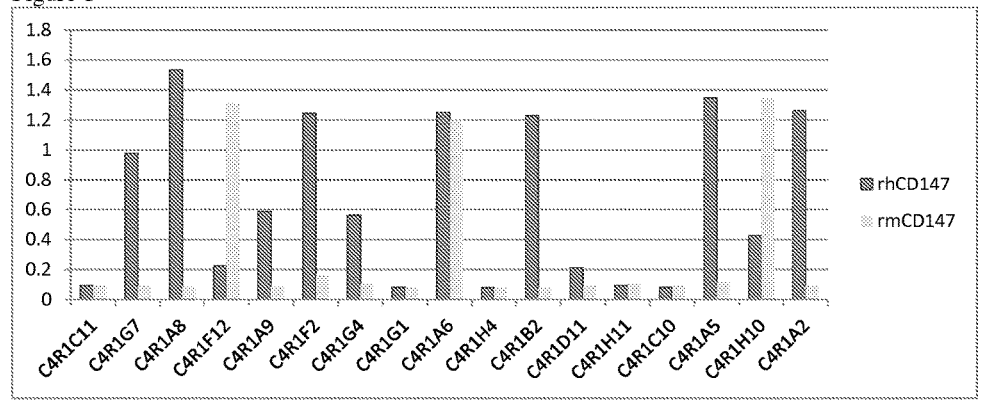
FIGS. 1 and 2 show that seven anti-CD147 antibodies can bind to both human or mouse CD147.

The present disclosure provides a fully human antibody of an IgG class that binds to a CD147 epitope with a binding affinity of $10^{-6}$M or less, that has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 26, SEQ ID NO. 28, SEQ ID NO. 30, SEQ ID NO. 34, SEQ ID NO. 36, SEQ ID NO. 38, SEQ ID NO. 41, SEQ ID NO. 43, SEQ ID NO. 46, SEQ ID NO. 48, SEQ ID NO. 50, SEQ ID NO. 53, SEQ ID NO. 56, SEQ ID NO. 59, SEQ ID NO. 62, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 35, SEQ ID NO. 37, SEQ ID NO. 39, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 52, SEQ ID NO. 54, SEQ ID NO. 55, SEQ ID NO. 57, SEQ ID NO. 58, SEQ ID NO. 60, SEQ ID NO. 61, SEQ ID NO. 63, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called C4R1A2 herein), SEQ ID NO. 3/SEQ ID NO. 4 (called C4R1A5 herein), SEQ ID NO. 5/SEQ ID NO. 6 (called C4R1A6 herein), SEQ ID NO. 7/SEQ ID NO. 8 (called C4R1A8 herein), SEQ ID NO. 9/SEQ ID NO. 10 (called C4R1A9 herein), SEQ ID NO. 11/SEQ ID NO. 12 (called C4R1B2 herein), SEQ ID NO. 13/SEQ ID NO. 14 (called C4R1C10 herein), SEQ ID NO. 15/SEQ ID NO. 16 (called C4R1C11 herein), SEQ ID NO. 17/SEQ ID NO. 18 (called C4R1C3 herein), SEQ ID NO. 19/SEQ ID NO. 20 (called C4R1D11 herein), SEQ ID NO. 21/SEQ ID NO. 22 (called C4R1F12 herein), SEQ ID NO. 13/SEQ ID NO. 25 (called C4R1G1 herein), SEQ ID NO. 26/SEQ ID NO. 27 (called C4R1G4 herein), SEQ ID NO. 28/SEQ ID NO. 29 (called C4R1G7 herein), SEQ ID NO. 30/SEQ ID NO. 31 (called C4R1H10 herein), SEQ ID NO. 13/SEQ ID NO. 32 (called C4R1H11 herein), SEQ ID NO. 13/SEQ ID NO. 33 (called C4R1H4 herein), SEQ ID NO. 34/SEQ ID NO. 35 (called C4sh1A1 herein), SEQ ID NO. 36/SEQ ID NO. 37 (called C4sh1A2 herein), SEQ ID NO. 38/SEQ ID NO. 39 (called C4sh1A3 herein), SEQ ID NO. 38/SEQ ID NO. 40 (called C4sh1A4 herein), SEQ ID NO. 41/SEQ ID NO. 42 (called C4sh1A5 herein), SEQ ID NO. 43/SEQ ID NO. 44 (called C4sh1A6 herein), SEQ ID NO. 38/SEQ ID NO. 45 (called C4sh1A9 herein), SEQ ID NO. 46/SEQ ID NO. 47 (called C4sh1B10 herein), SEQ ID NO. 48/SEQ ID NO. 49 (called C4sh1B11 herein), SEQ ID NO. 50/SEQ ID NO. 51 (called C4sh1B2 herein), SEQ ID NO. 38/SEQ ID NO. 52 (called C4sh1C10 herein), SEQ ID NO. 53/SEQ ID NO. 54 (called C4sh1C5 herein), SEQ ID NO. 41/SEQ ID NO. 54 (called C4sh1C6 herein), SEQ ID NO. 56/SEQ ID NO. 57 (called C4sh1E10 herein), SEQ ID NO. 38/SEQ ID NO. 58 (called C4sh1E12 herein), SEQ ID NO. 59/SEQ ID NO. 60 (called C4sh1F11 herein), SEQ ID NO. 38/SEQ ID NO. 61 (called C4sh1G4 herein), SEQ ID NO. 62/SEQ ID NO. 63 (called C4sh1H9 herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 26, SEQ ID NO. 28, SEQ ID NO. 30, SEQ ID NO. 34, SEQ ID NO. 36, SEQ ID NO. 38, SEQ ID NO. 41, SEQ ID NO. 43, SEQ ID NO. 46, SEQ ID NO. 48, SEQ ID NO. 50, SEQ ID NO. 53, SEQ ID NO. 56, SEQ ID NO. 59, SEQ ID NO. 62, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 35, SEQ ID NO. 37, SEQ ID NO. 39, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 52, SEQ ID NO. 54, SEQ ID NO. 55, SEQ ID NO. 57, SEQ ID NO. 58, SEQ ID NO. 60, SEQ ID NO. 61, SEQ ID NO. 63, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 13/SEQ ID NO. 25, SEQ ID NO. 26/SEQ ID NO. 27, SEQ ID NO. 28/SEQ ID NO. 29, SEQ ID NO. 30/SEQ ID NO. 31, SEQ ID NO. 13/SEQ ID NO. 32, SEQ ID NO. 13/SEQ ID NO. 33, SEQ ID NO. 34/SEQ ID NO. 35, SEQ ID NO. 36/SEQ ID NO. 37, SEQ ID NO. 38/SEQ ID NO. 39, SEQ ID NO. 38/SEQ ID NO. 40, SEQ ID NO. 41/SEQ ID NO. 42, SEQ ID NO. 43/SEQ ID NO. 44, SEQ ID NO. 38/SEQ ID NO. 45, SEQ ID NO. 46/SEQ ID NO. 47, SEQ ID NO. 48/SEQ ID NO. 49, SEQ ID NO. 50/SEQ ID NO. 51, SEQ ID NO. 38/SEQ ID NO. 52, SEQ ID NO. 53/SEQ ID NO. 54, SEQ ID NO. 41/SEQ ID NO. 54, SEQ ID NO. 56/SEQ ID NO. 57, SEQ ID NO. 38/SEQ ID NO. 58, SEQ ID NO. 59/SEQ ID NO. 60, SEQ ID NO. 38/SEQ ID NO. 61, SEQ ID NO. 62/SEQ ID NO. 63, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 26, SEQ ID NO. 28, SEQ ID NO. 30, SEQ ID NO. 34, SEQ ID NO. 36, SEQ ID NO. 38, SEQ ID NO. 41, SEQ ID NO. 43, SEQ ID NO. 46, SEQ ID NO. 48, SEQ ID NO. 50, SEQ ID NO. 53, SEQ ID NO. 56, SEQ ID NO. 59, SEQ ID NO. 62, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 35, SEQ ID NO. 37, SEQ ID NO. 39, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 52, SEQ ID NO. 54, SEQ ID NO. 55, SEQ ID NO. 57, SEQ ID NO. 58, SEQ ID NO. 60, SEQ ID NO. 61, SEQ ID NO. 63, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 13/SEQ ID NO. 25, SEQ ID NO. 26/SEQ ID NO. 27, SEQ ID NO. 28/SEQ ID NO. 29, SEQ ID NO. 30/SEQ ID NO. 31, SEQ ID NO. 13/SEQ ID NO. 32, SEQ ID NO. 13/SEQ ID NO. 33, SEQ ID NO. 34/SEQ ID NO. 35, SEQ ID NO. 36/SEQ ID NO. 37, SEQ ID NO. 38/SEQ ID NO. 39, SEQ ID NO. 38/SEQ ID NO. 40, SEQ ID NO. 41/SEQ ID NO. 42, SEQ ID NO. 43/SEQ ID NO. 44, SEQ ID NO. 38/SEQ ID NO. 45, SEQ ID NO. 46/SEQ ID NO. 47, SEQ ID NO. 48/SEQ ID NO. 49, SEQ ID NO. 50/SEQ ID NO. 51, SEQ ID NO. 38/SEQ ID NO. 52, SEQ ID NO. 53/SEQ ID NO. 54, SEQ ID NO. 41/SEQ ID NO. 54, SEQ ID NO. 56/SEQ ID NO. 57, SEQ ID NO. 38/SEQ ID NO. 58, SEQ ID NO. 59/SEQ ID NO. 60, SEQ ID NO. 38/SEQ ID NO. 61, SEQ ID NO. 62/SEQ ID NO. 63, and combinations thereof.

The present disclosure further provides a method for treating rheumatoid arthritis, experimental lung injury, atherosclerosis, chronic liver disease induced by hepatitis C virus, ischemic myocardial injury and heart failure, comprising administering an anti-CD147 polypeptide, wherein the anti-CD147 polypeptide is selected from the group consisting of a fully human antibody of an IgG class that binds to a CD147 epitope with a binding affinity of at least $10^{-6}$ M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 26, SEQ ID NO. 28, SEQ ID NO. 30, SEQ ID NO. 34, SEQ ID NO. 36, SEQ ID NO. 38, SEQ ID NO. 41, SEQ ID NO. 43, SEQ ID NO. 46, SEQ ID NO. 48, SEQ ID NO. 50, SEQ ID NO. 53, SEQ ID NO. 56, SEQ ID NO. 59, SEQ ID NO. 62, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 35, SEQ ID NO. 37, SEQ ID NO. 39, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 52, SEQ ID NO. 54, SEQ ID NO. 55, SEQ ID NO. 57, SEQ ID NO. 58, SEQ ID NO. 60, SEQ ID NO. 61, SEQ ID NO. 63, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 26, SEQ ID NO. 28, SEQ ID NO. 30, SEQ ID NO. 34, SEQ ID NO. 36, SEQ ID NO. 38, SEQ ID NO. 41, SEQ ID NO. 43, SEQ ID NO. 46, SEQ ID NO. 48, SEQ ID NO. 50, SEQ ID NO. 53, SEQ ID NO. 56, SEQ ID NO. 59, SEQ ID NO. 62, and combinations thereof, and that has the light chain variable domain sequence that is at least 95% identical to the amino acid sequence consisting SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 35, SEQ ID NO. 37, SEQ ID NO. 39, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 52, SEQ ID NO. 54, SEQ ID NO. 55, SEQ ID NO. 57, SEQ ID NO. 58, SEQ ID NO. 60, SEQ ID NO. 61, SEQ ID NO. 63, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 26, SEQ ID NO. 28, SEQ ID NO. 30, SEQ ID NO. 34, SEQ ID NO. 36, SEQ ID NO. 38, SEQ ID NO. 41, SEQ ID NO. 43, SEQ ID NO. 46, SEQ ID NO. 48, SEQ ID NO. 50, SEQ ID NO. 53, SEQ ID NO. 56, SEQ ID NO. 59, SEQ ID NO. 62, and combinations thereof, and that has the light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 35, SEQ ID NO. 37, SEQ ID NO. 39, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 52, SEQ ID NO. 54, SEQ ID NO. 55, SEQ ID NO. 57, SEQ ID NO. 58, SEQ ID NO. 60, SEQ ID NO. 61, SEQ ID NO. 63, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 13/SEQ ID NO. 25, SEQ ID NO. 26/SEQ ID NO. 27, SEQ ID NO. 28/SEQ ID NO. 29, SEQ ID NO. 30/SEQ ID NO. 31, SEQ ID NO. 13/SEQ ID NO. 32, SEQ ID NO. 13/SEQ ID NO. 33, SEQ ID NO. 34/SEQ ID NO. 35, SEQ ID NO. 36/SEQ ID NO. 37, SEQ ID NO. 38/SEQ ID NO. 39, SEQ ID NO. 38/SEQ ID NO. 40, SEQ ID NO. 41/SEQ ID NO. 42, SEQ ID NO. 43/SEQ ID NO. 44, SEQ ID NO. 38/SEQ ID NO. 45, SEQ ID NO. 46/SEQ ID NO. 47, SEQ ID NO. 48/SEQ ID NO. 49, SEQ ID NO. 50/SEQ ID NO. 51, SEQ ID NO. 38/SEQ ID NO. 52, SEQ ID NO. 53/SEQ ID NO. 54, SEQ ID NO. 41/SEQ ID NO. 54, SEQ ID NO. 56/SEQ ID NO. 57, SEQ ID NO. 38/SEQ ID NO. 58, SEQ ID NO. 59/SEQ ID NO. 60, SEQ ID NO. 38/SEQ ID NO. 61, SEQ ID NO. 62/SEQ ID NO. 63, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 13/SEQ ID NO. 25, SEQ ID NO. 26/SEQ ID NO. 27, SEQ ID NO. 28/SEQ ID NO. 29, SEQ ID NO. 30/SEQ ID NO. 31, SEQ ID NO. 13/SEQ ID NO. 32, SEQ ID NO. 13/SEQ ID NO. 33, SEQ ID NO. 34/SEQ ID NO. 35, SEQ ID NO. 36/SEQ ID NO. 37, SEQ ID NO. 38/SEQ ID NO. 39, SEQ ID NO. 38/SEQ ID NO. 40, SEQ ID NO. 41/SEQ ID NO. 42, SEQ ID NO. 43/SEQ ID NO. 44, SEQ ID NO. 38/SEQ ID NO. 45, SEQ ID NO. 46/SEQ ID NO. 47, SEQ ID NO. 48/SEQ ID NO. 49, SEQ ID NO. 50/SEQ ID NO. 51, SEQ ID NO. 38/SEQ ID NO. 52, SEQ ID NO. 53/SEQ ID NO. 54, SEQ ID NO. 41/SEQ ID NO. 54, SEQ ID NO. 56/SEQ ID NO. 57, SEQ ID NO. 38/SEQ ID NO. 58, SEQ ID NO. 59/SEQ ID NO. 60, SEQ ID NO. 38/SEQ ID NO. 61, SEQ ID NO. 62/SEQ ID NO. 63, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 13/SEQ ID NO. 25, SEQ ID NO. 26/SEQ ID NO. 27, SEQ ID NO. 28/SEQ ID NO. 29, SEQ ID NO. 30/SEQ ID NO. 31, SEQ ID NO. 13/SEQ ID NO. 32, SEQ ID NO. 13/SEQ ID NO. 33, SEQ ID NO. 34/SEQ ID NO. 35, SEQ ID NO. 36/SEQ ID NO. 37, SEQ ID NO. 38/SEQ ID NO. 39, SEQ ID NO. 38/SEQ ID NO. 40, SEQ ID NO. 41/SEQ ID NO. 42, SEQ ID NO. 43/SEQ ID NO. 44, SEQ ID NO. 38/SEQ ID NO. 45, SEQ ID NO. 46/SEQ ID NO. 47, SEQ ID NO. 48/SEQ ID NO. 49, SEQ ID NO. 50/SEQ ID NO. 51, SEQ ID NO. 38/SEQ ID NO. 52, SEQ ID NO. 53/SEQ ID NO. 54, SEQ ID NO. 41/SEQ ID NO. 54, SEQ ID NO. 56/SEQ ID NO. 57, SEQ ID NO. 38/SEQ ID NO. 58, SEQ ID NO. 59/SEQ ID NO. 60, SEQ ID NO. 38/SEQ ID NO. 61, SEQ ID NO. 62/SEQ ID NO. 63, and combinations thereof.

Preferably, the method is for treating rheumatoid arthritis, experimental lung injury, atherosclerosis, chronic liver disease induced by hepatitis C virus, ischemic myocardial injury and heart failure.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, $5^{th}$ Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or VL domain (U.S. Pat. Nos. 6,846,634; 6,696,245, US App. Pub. 20/0202512; 2004/0202995; 2004/0038291; 2004/0009507; 20 03/0039958, and Ward et al., *Nature* 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-CD147 antibody. In another embodiment, all of the CDRs are derived from a human anti-CD147 antibody. In another embodiment, the CDRs from more than one human anti-CD147 antibodies are mixed and matched in a chimeric antibody. For instance, a chimeric antibody may comprise a CDR1 from the light chain of a first human antibody, a CDR2 and a CDR3 from the light chain of a second human anti-CD147 antibody, and the CDRs from the heavy chain from a third anti-CD147 antibody. Other combinations are possible.

Further, the framework regions may be derived from one of the same anti-CD147 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind CD147).

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, *Science* 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human CD147) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad Sci. USA.* 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3):512-38; and Sharp et al. *Yeast.* 1991 7(7):657-78.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in E. coli as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

CD147-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis. The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. Biochemistry. 2001 31; 40(30):8868-76.

In one embodiment, modified forms of the subject soluble polypeptides comprise linking the subject soluble polypeptides to nonproteinaceous polymers. In one embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-O(CH_2CH_2O)_n-CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., Bioconjugate Chem. 6 (1995) 62-69).

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Formulations and Modes of Administration

The present disclosure features method for treating or preventing the S. aureus infection comprising administering an anti-CD147 polypeptide. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

Exemplary Uses

A CD147 binding polypeptide can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for treating CD147-expressing tumors, including hepatocellular carcinomas and squamous carcinomas, and non-oncology diseases selected from the group consisting of rheumatoid arthritis, experimental lung injury, atherosclerosis, chronic liver disease induced by hepatitis C virus, ischemic myocardial injury and heart failure.

In certain embodiments, the subject anti-CD147 antibodies agents of the invention can be used alone.

In certain embodiments, the binding polypeptides of fragments thereof can be labeled or unlabeled for diagnostic purposes. Typically, diagnostic assays entail detecting the formation of a complex resulting from the binding of a binding polypeptide to CD147. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a CD147 protein is combined with the subject binding polypeptides, binding occurs between the binding polypeptides and the CD147 protein. In one embodiment, a sample containing cells expressing a CD147 protein (e.g., endothelial cells) is combined with the subject antibodies, and binding occurs between the binding polypeptides and cells bearing a CD147 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a CD147 protein in a biological sample can also be prepared. Such kits will include a CD147 binding polypeptide which binds to a CD147 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

The following terms, unless otherwise indicated, shall be understood to have the following meanings:

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-EGFR antibodies disclosed herein are characterized by their variable domain region sequences in the heavy $V_H$ and light $V_L$ amino acid sequences. The preferred antibody is A6 which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human CD147) if it binds to the antigen with a dissociation constant of 100 nanomolar or less.

An "antigen binding domain, "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

A "host cell" is a cell that can be used to express a nucleic acid. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, Cytotechnology 28:31) or CHO strain DX-B11, which is deficient in DHFR (Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (McMahan et al., 1991, EMBO J. 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

Antigen binding proteins (e.g., antibodies, antibody fragments, antibody derivatives, antibody muteins, and antibody variants) are polypeptides that bind to CD147.

Oligomers that contain one or more antigen binding proteins may be employed as CD147 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have CD147 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, Proc. Natl. Acad. Sci. USA 88:10535; Byrn et al., 1990, Nature 344:677; and Hollenbaugh et al., 1992 "Construction of Immunoglobulin Fusion Proteins", in Current Protocols in Immunology, Suppl. 4, pages 10.19.1-10.19.11.

One embodiment is directed to a dimer comprising two fusion proteins created by fusing a CD147 binding fragment of an anti-CD147 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, FEBS Letters 344:191. The use of a modified leucine zipper that allows for stable trimerization of a heterologous protein fused thereto is described in Fanslow et al., 1994, Semin. Immunol. 6:267-78. In one approach, recombinant fusion proteins comprising an anti-CD147 antibody fragment or derivative fused to a leucine zipper peptide are expressed in suitable host cells, and the soluble oligomeric anti-CD147 antibody fragments or derivatives that form are recovered from the culture supernatant.

Antigen-binding fragments of antigen binding proteins of the invention may be produced by conventional techniques. Examples of such fragments include, but are not limited to, Fab and F(ab')$_2$ fragments.

The present disclosure provides monoclonal antibodies that bind to CD147. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen binding proteins directed against CD147 can be used, for example, in assays to detect the presence of CD147 polypeptides, either in vitro or in vivo. The antigen binding proteins also may be employed in purifying CD147 proteins by immunoaffinity chromatography. Blocking antigen binding proteins can be used in the methods disclosed herein. Such antigen binding proteins that function as CD147 antagonists may be employed in treating any CD147-induced condition, including but not limited to various cancers.

Antigen binding proteins may be employed in an in vitro procedure, or administered in vivo to inhibit CD147-induced biological activity. Disorders caused or exacerbated (directly or indirectly) by the proteolytic activation of CD147, examples of which are provided herein, thus may be treated. In one embodiment, the present invention provides a therapeutic method comprising in vivo administration of a CD147 blocking antigen binding protein to a mammal in need thereof in an amount effective for reducing a CD147-induced biological activity.

Antigen binding proteins include fully human monoclonal antibodies that inhibit a biological activity of CD147.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of CD147 bound thereto. Polypeptides contemplated for use herein include substantially homogeneous recombinant mammalian anti-CD147 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-CD147 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSCP→CPPCP) in the hinge region (Bloom et al., 1997, *Protein Science* 6:407) to alleviate a tendency to form intra-H chain disulfide bonds that can lead to heterogeneity in the IgG4 antibodies.

In particular embodiments, antigen binding proteins of the present invention have a binding affinity ($K_a$) for CD147 of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present disclosure provides an antigen binding protein that has a low dissociation rate from CD147. In one embodiment, the antigen binding protein has a $K_{off}$ of $1 \times 10^{-4}$ to $^{-1}$ or lower. In another embodiment, the $K_{off}$ is $5 \times 10^{-5}$ to $^{-1}$ or lower. In another embodiment, the $K_{off}$ is substantially the same as an antibody described herein. In another embodiment, the antigen binding protein binds to CD147 with substantially the same $K_{off}$ as an antibody described herein.

In another aspect, the present disclosure provides an antigen binding protein that inhibits an activity of CD147. In one embodiment, the antigen binding protein has an $IC_{50}$ of 1000 nM or lower. In another embodiment, the $IC_{50}$ is 100 nM or lower, in another embodiment, the $IC_{50}$ is 10 nM or lower. In another embodiment, the $IC_{50}$ is substantially the same as that of an antibody described herein in the Examples. In another embodiment, the antigen binding protein inhibits an activity of CD147 with substantially the same $IC_{50}$ as an antibody described herein.

In another aspect, the present disclosure provides an antigen binding protein that binds to human CD147 expressed on the surface of a cell and, when so bound, inhibits CD147 signaling activity in the cell without causing a significant reduction in the amount of CD147 on the surface of the cell. Any method for determining or estimating the amount of CD147 on the surface and/or in the interior of the cell can be used. In other embodiments, binding of the antigen binding protein to the CD147-expressing cell causes less than about 75%, 50%, 40%, 30%, 20%, 15%, 10%, 5%, 1%, or 0.1% of the cell-surface CD147 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of CD147, or to an epitope of CD147 and an epitope of another molecule, via two different antigen binding sites or regions. Moreover, bispecific antigen binding protein as disclosed herein can comprise a CD147 binding site from one of the herein-described antibodies and a second CD147 binding region from another of the herein-described antibodies, including those described herein by reference to other publications. Alternatively, a bispecific antigen binding protein may comprise an antigen binding site from one of the herein described antibodies and a second antigen binding site from another CD147 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TIR or TIR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

All identified mAbs were crossreactive with recombinant human and murine CD147 proteins (commercially available from R&D Systems or Sino Biologics) using ELISA screening. Using an OctetRed instrument, the disclosed mAbs were evaluated for affinity against recombinant human CD147 protein and ranked based on the affinity data. The disclosed clones demonstrated at least single digit nanomolar affinity against human CD147.

Preferably, the disclosed antibodies are administered by inhalation, but aerosolization of full IgG antibodies may prove limiting due to their molecular size (~150 kDa). To maximize available commercial aerosolization devices, smaller Fab fragments may be required. In this case, we may also need to generate Fab fragments from the parental IgG molecules. Therefore, we will perform initial studies using standard enzyme-based digestion methodologies for the generation of Fab fragments, which will then be characterized in parallel with full IgG molecules.

Example 1

Figure 2:
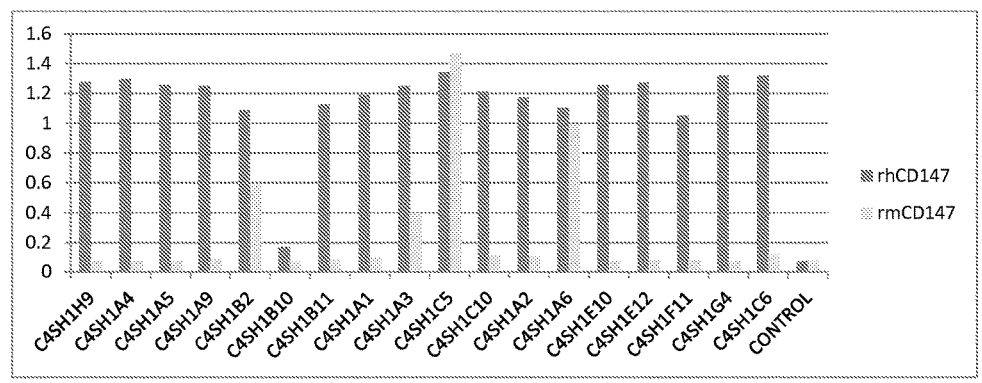
Figure 4:
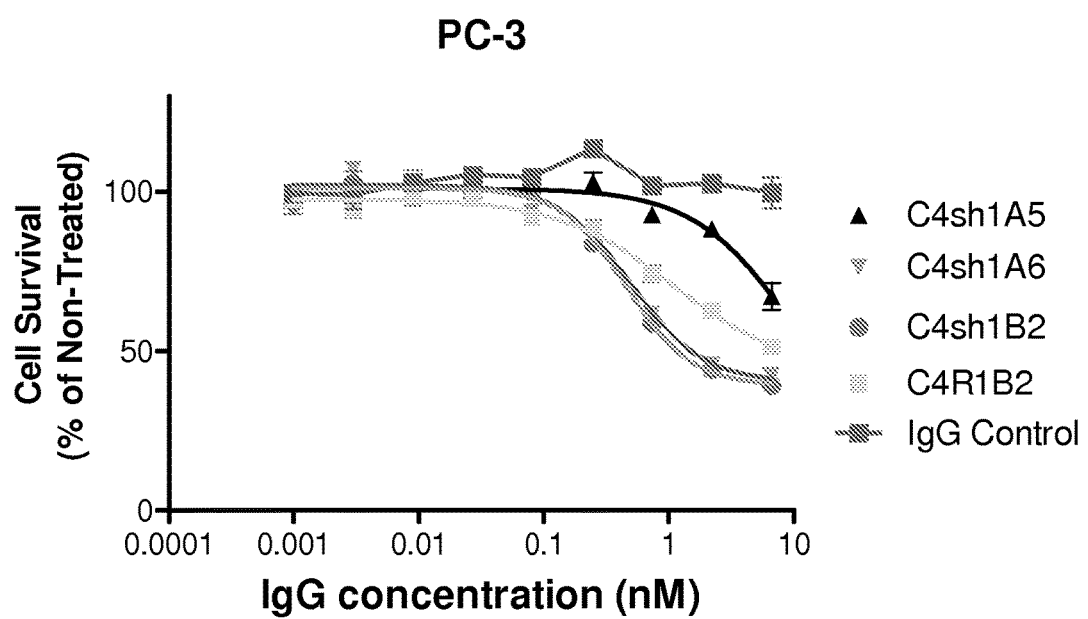
FIG. 4 illustrate the cytotoxic potential of anti-CD147 antibodies when complexed with Protein G-DM1 molecules.

This example provides an analysis of the cross-reactivity of CD147 binders to recombinant mouse CD147. Briefly, an NI-NTA ELISA plate was captured with the recombinant human or mouse CD147, and then incubated with the anti-CD147 antibodies. Binding of antibody was measured. FIGS. 1 and 2 show that seven anti-CD147 antibodies can bind to both human or mouse CD147.

Example 2

This example illustrates the binding of anti-CD147 antibodies to endogenous human CD147 expressed on human cancer cells, as assayed by flow cytometry. $EC_{50}$ values for antibodies were determined as follows.

CD147 expressing cells (PC-3, A549, or K562) were harvested with enzyme-free Cell Dissociation Buffer (GIBCO) and transferred to V-Bottom 96 well-plates (50, 000 cells/well). Cells were incubated on ice for 45 min with serial dilutions of anti-CD147 antibodies in FACS buffer (PBS+2% FBS). After 2 washes in FACS buffer, a 1:1000 dilution of Phycoerythrin conjugated anti-Human IgG (γ-chain specific) was added and incubated for 20 min. Following a final wash, fluorescence intensity was measured on an Intellicyt High Throughput Flow Cytometer (HTFC). Data were analyzed using Graphpad Prism software and non-linear regression fit. Data points are shown as the median fluorescence intensity (MFI) of positively labeled cells +/−Standard Error. $EC_{50}$ values are reported as the concentration of antibody to achieve 50% of maximal CD147 antibodies binding to CD147 expressing cells.

As shown in FIGS. 3A-C and Table 1, selected antibodies bound to cellular CD147 expressing with variable affinities, and displayed $EC_{50}$ values ranging from 0.6 to 168 nM. Table 1: Table 1 summarizes the binding characteristics ($EC_{50}$, in NanoMol·L$^{-1}$) of anti-CD147 antibodies to cells either expressing CD147.

TABLE 1

| Cell Line | Anti-CD147 Clone | | | |
|---|---|---|---|---|
| (EC50, nM) | C4sh1A5 | C4sh1A6 | C4sh1B2 | C4R1B2 |
| A549 | 8.73 | 35.93 | 3.73 | 83.76 |
| K562 | 5.735 | 0.6 | 1.55 | 168.5 |
| PC-3 | 5.2 | >100 | 4.5 | >100 |

This example illustrates in vitro data showing the assessment of anti-CD147 antibodies in a cytotoxicity assay using secondary antibody-drug conjugate technique (*). This example demonstrates the potential of anti-CD147 to be used as antibody drug conjugates.

*"Secondary Antibody-Drug Conjugates As Tools for ADC Discovery". Helen Mao, Poster (IBC 24th Annual, 2013).

CD147 expressing cells (A549 or PC-3) were harvested with enzyme-free Cell Dissociation Buffer (GIBCO), seeded into white 96-Well Clear Bottom plates (1,000 cells/well in 90 ul) and allowed to adhere overnight at 37° C. Antibodies were pre-complexed with ProteinG-DM1 (Concortis Biosystems) in cell culture media, at a 1:4 molar ratio. After 10 min at room temperature, serial dilutions of the antibody-ProteinG-DM1 complex were prepared in cell culture media, incubated 10 more minutes at room temperature, and added to cells (10 µl/well) in triplicate. After 96H incubation at 37° C., cells proliferation was analyzed as follows: 100 µl of Cell Titer Glo buffer (Promega) was added to each well. Plates were incubated with shaking at room temperature for 20 min. Luminescence signal was then measured on a Flexstation 3 plate reader (Molecular Device). Data were reported as relative Luminescent Units. Dose-response curves were generated in GraphPad prism, and IC50 values were calculated using non-linear regression fit (log(inhibitor) vs. response—Variable slope equation).

The results shown in FIG. 2, indicate that anti-CD147 antibodies, particularly C4sh1A6 and C4sh1B2, can induce cell killing when complexed with a cytotoxin such as DM-1. This illustrates the potential of CD147 antibodies as antibody-drug conjugates.

| Sequence Listing | | |
|---|---|---|
| | Heavy chain variable domain region | Light chain variable domain region |
| C4R1A2 | VQLVQSGAEVKKPGASVKVS CKASGYTFTGYYMHWVRQAP GQGLEWMGWINPNSGGTNYA QKFQGRVTMTRDTSASTAYM ELSGLRSEDTAVYYCARGNL FIDYWGQGTLVTVSS SEQ ID NO. 1 | LPVLTQPASVSGSPGQSITI SCTGTSSDVGSYNLVSWYQQ HPGKAPKLMIYDVSKRPSGV SNRFSGSKSGNTASLTISGL QAEDEADYYCSSYTSSSTFV FGGGTKLTVL SEQ ID NO. 2 |
| C4R1A5 | EVQLVESGAEVKKPGASVRV SCRASGYTFTNYAISWVRQA PGQGLEWMGWISTYNGNTLY AQKLQGRVTMTTDTSTSTAY MELRSLRSDDTAVYYCARDT DTYYFDYWGQGTLVTVSS SEQ ID NO. 3 | QPVLTQPASVSGSPGQSITI SCTGTSSDVGGYNYVSWYQQ HPDKPPKLIIYYVSNRPSGV SNRFSGSKSGNTASLTISGL QAEDEADYYCASYRSNTNYV FGTGTKVTVL SEQ ID NO. 4 |
| C4R1A6 | EVQLLESGAEVKKPGASVKV SCKASGYTFTSHYMHWVRQA PGQGLEWMGVINPSGGSTSY AQKFQGRVTMTRDTSTSTVY MDLSSLRSEDTAVYYCARRS EAYYHGMDVWGQGTTVTVSS SEQ ID NO. 5 | QSVLTQPPSASGTPGQRVTI SCSGSSSNIGSNYVYWYQQF PGTTPKLLIYRNNQRPSGVP DRFSGSKSATSASLAISGLR SEDEADYYCAAWDDSLSGWV FGGGTKLTVL SEQ ID NO. 6 |
| C4R1A8 | EVQLVESGAEVKKPGASVRV SCRASGYTFTNYAISWVRQA PGQGLEWMGWISTYNGNTLY AQKLQGRVTMTTDTSTSTAY MELRSLRSDDTAVYYCARDT DTYYFDYWGQGTLVTVSS SEQ ID NO. 7 | QAGLTQPASVSGSPGQSITI SCTGTSSDVGGYNYVSWYQQ HPGKAPKLMIYNVTKRPSGV SNRFSGSKSGNTASLTISGL QAEDEADYYCSSYTSGTTLS VFGTGTKLTVL SEQ ID NO. 8 |
| C4R1A9 | EVQLVESGAEVKKPGASVKV SCKASGYTFTGYYMHWVRQA PGQGLEWMGWINPNSGGTNY AQKFQGRVTMTRDTSISTAY MELSSLRSDDTAVYYCARGA TGGYGMDVWGQGTTVTVSS SEQ ID NO. 9 | QSALTQPRSVSGSPGQSVTI SCTGTSNDVGAYNYVSWYQQ HPAKAPKLMIYGVTKRPSGV PDRFSGANSGNTATLTITRV EAGDEADYFCQVWERSSGQY VFGTGTKLTVL SEQ ID NO. 10 |
| C4R1B2 | QVQLVQSGAEVKKPGASVKV SCKASGYGFTSYAIHWLRQA PGQRLEWMGWINPGNGNTKY SQKFQGRVTITRDTSATTAY MELTSLRSEDSDTAVYYCAR DLDGGSFDHWGQGTLVTVSS SEQ ID NO. 11 | QSVVTQPASVSGSPGQSITI SCTGTSSDVGSYNLVSWYQQ HPGKAPKLMIYDVTNRPSGV SNRFSGSKSGNTASLTISGL QAEDEADYYCSSYTRSSYV FGTGTKVTVL SEQ ID NO. 12 |
| C4R1C10 | QVQLVQSGAEVKKPGASVKI SCKASGYTFTTYWIHWVRQA PGQGPEWMGLIKPSSGSTTY PQKFQGRVTMTRDTSTSTVY MELSSLRSEDTAVYYCARLE GIGAASNDWGQGTLVTVSS SEQ ID NO. 13 | QAVVTQEPSLTVSPGGTVTL TCGSSTGAVTSGHYPYWFQQ KPGQAPRTLIYDTSNKHSWT PARFSGSLLGGKAALTLSGA QPEDEAEYYCLLSYSGARVF GTGTKVTVL SEQ ID NO. 14 |
| C4R1C11 | QVQLVQSGAEVKKPGASVKI SCKASGYTFTTYWIHWVRQA PGQGPEWMGLIKPSSGSTTY PQKFQGRVTMTRDTSTSTVY MELSSLRSEDTAVYYCARLE GIGAASNDWGQGTLVTVSS SEQ ID NO. 15 | QTVVTQEPSLTVSPGGTVTL TCGSSTGDVTSGHYPYWFQQ KPGQAPRTLIYDTSNKHSWT PARFSASLLGGKAALTLSGA QPEDEADYYCLLAYSEVRVF GGGTQLTVL SEQ ID NO. 16 |
| C4R1C3 | QVQLVQSGSELKKPGASVKV SCKASGYSFRSYDINWVRQA PGQGLEWMGFLNPSDGGTTY AQKFQGRVTVTSDTSTSTVY MELSSLRSENTAVYYCARVG ITSTETRAEYFQHWGQGTLV TVSS SEQ ID NO. 17 | QSVLTQPPSASGSPGQSVTI SCTGSASDIGHSFYVSWYRQ YPGKAPDLLIFQVNQRPSGV PNRFSASKSGNTASLTVSGL QIEDEADYYCSSYAGGTSIV FGSGTKLTVL SEQ ID NO. 18 |
| C4R1D11 | QVQLVQSGAEVKKPGASVKL SCKASGYTFTRYWVHWVRQA PGQGPEWMGLIKPRDGATTY | QTVVTQEPSLTVSPGGTVTL TCGSSTGAVTSGHYPYWFQQ KPGQPPRTLIYDTSNKHSWT |

Sequence Listing

| | Heavy chain variable domain region | Light chain variable domain region |
|---|---|---|
| | AQKFQGRVTLTRDTSTTTVY MELTSLRSEDTGIYYCGLLE GDDAFDWGQGTMVTVSS SEQ ID NO. 19 | PARFSGSLLGGKAALTLSGA QPEDEAEYYCLLSYSGARVF GGGTKLTVL SEQ ID NO. 20 |
| C4R1F12 | QVQLVESGAEVKKPGASVKV SCKASGYTFTSYYMHWVRQA PGQGLEWMGIINPSGGSTSY AQKFQGRVTMTRDTSTSTVY MELSSLRSEDTAVYYCARES YGSGSLDYWGQGTLVTVSS SEQ ID NO. 21 | ETTLTQSPATLSVSPGERAT LSCRASQSVSSYLAWYQQKP GQAPRLLIYDASNRATGIPA RFSGSGSGTDFTLTISSLEP EDFAVYYCQQRSNWPQITFG QGTRLEIK SEQ ID NO. 22 |
| C4R1F2 | QVQLVQSGGGVVRPGGSLRL SCAASGFTFGDYGMSWVRQA PGRGLEWVAGIIWNGGTTGY ADSVKGRFTISRDNAKNSLY LEMNSLRAEDTAVYYCTRDL NYYISGDYYDAFDIWGQGTM VTVSS SEQ ID NO. 23 | SSELTQDPAVSVALGQTVRI TCQGDSLRSYYASWYQQKPG QAPVLVIYGKNNRPSGIPDR FSGSSSGNTASLTITGAQAE DEADYYCNSRDSSGNHRVFG GGTKLTVL SEQ ID NO. 24 |
| C4R1G1 | QVQLVQSGAEVKKPGASVKI SCKASGYTFTTYWIHWVRQA PGQGPEWMGLIKPSSGSTTY PQKFQGRVTMTRDTSTSTVY MELSSLRSEDTAVYYCARLE GIGAASNDWGQGTLVTVSS SEQ ID NO. 13 | QTVVTQEPSLTVSPGGTVTL TCGSDTGAVNSGHYPYWFQQ KPGQAPRALIYDTGNKHSWT PARFSGSLLGGKAALTLSGA QPEDEAEYYCLLSYSGTRIF GGGTKLTVL SEQ ID NO. 25 |
| C4R1G4 | EVQLLESGAEVKKPGASVKV SCKASGYTFTGYYMHWVRQA PGQGLEWMGWINPNSGGTNY AQKFQGRVTMTRDTSISTAY MELSRLRSDDTAVYYCARPK GHSGGWYAFDIWGQGTMVTV SS SEQ ID NO. 26 | QSVLTQPPSASGTPGQRVTI SCSGSSSNIGRRAVNWYQQL PGTAPKLLIYDNDRRPSGIP DRFSGSKSGTSATLGITELQ TGDEADYYCGTWDTNLSAGL FGGGTKLTVL SEQ ID NO. 27 |
| C4R1G7 | QVQLQQSGPGLVKPAQTLSL TCAISGDSVSSSRAAWNWIR QSPSRGLEWLGRTFYRSRWN NEYAETVKSRITINPDTSTN HFSLQLTSVSPEDTAIYYCA RGGGNFDSWGQGTLVTVSS SEQ ID NO. 28 | QSVLTQPPSVSAAPGQKVTI SCSGSSSNIGNNYVSWYQQL PGTAPKLLIYDNNKRPSGIP DRFSGSKSGTSATLGITGLQ TGDEADYYCGTWDSSLSAGD VVFGGGTKLTVL SEQ ID NO. 29 |
| C4R1H10 | QVQLVQSGAEVKKPGASVKV SCKASGYTFTSYYMHWVRQA PGQGLEWMGIINPSGGSTSY AQKFQGRVTMTRDTSTSTVY MELSSLRSEDTAVYYCARES EDSIAFDIWGQGTMVTVSS SEQ ID NO. 30 | AIQLTQSPGTLSLAPGERAT LSCRASQSVSSSYIAWYQQR PGQAPRLLIYGASNRATDIP ARFIGSGSGTDFTLTISSLE PEDFAVYYCQQRSNWPRNTF GQGTRLEIK SEQ ID NO. 31 |
| C4R1H11 | QVQLVQSGAEVKKPGASVKI SCKASGYTFTTYWIHWVRQA PGQGPEWMGLIKPSSGSTTY PQKFQGRVTMTRDTSTSTVY MELSSLRSEDTAVYYCARLE GIGAASNDWGQGTLVTVSS SEQ ID NO. 13 | QTVVTQEPSLTVSPGGTVTL TCGSNTGAVTSGHYPYWFQQ KPGQAPRTLIYDATNKQSWT PARFSGSLLGDKAALTLSGA QPEDEAEYYCLLSYSGVRVF GGGTKLTVL SEQ ID NO. 32 |
| C4R1H4 | QVQLVQSGAEVKKPGASVKI SCKASGYTFTTYWIHWVRQA PGQGPEWMGLIKPSSGSTTY PQKFQGRVTMTRDTSTSTVY MELSSLRSEDTAVYYCARLE GIGAASNDWGQGTLVTVSS SEQ ID NO. 13 | QTVVTQEPSLTVSPGGTVTL TCGSSTGAVTSGHYPYWFQQ KPGQAPRTLIYDTSNKHSWT PARFSGSLLGGKAALTLSGA QPEDEADYFCLLSSSGARVF GGGTKLTVL SEQ ID NO. 33 |
| C4sh1A1 | QVQLVQSGAEVRKPGASVMV SCKASGYPFTSYAIHWLRQA PGQSLEWMGWIKPANGDITY SQKFQGRVTITGDISATTAY MELSSLRSEDTAMYYCTKGG GGYFDWGQGTLVTVSS SEQ ID NO. 34 | SQVLTQPRSVSGSPGQSVT ISCTGTSSDVGGYNLVSWYQ QHPGKAPKLMIYDVHKRPSG TSTRFSGSKSGNTASLTISG LQAEDEADYYCSSYRSGSTY VFGTGTKVTVL SEQ ID NO. 35 |
| C4sh1A2 | QVQLVQSGAEVKKPGESLRI SCQGSGYSFINHWISWVRQM PGKGLEWLGRIDPSDSYTNY SPSVQGHVTISVDKSISTAY LQWSSLKASDTAIYYCARHD RNVYFDPWGQGTLVTVSS SEQ ID NO. 36 | SYELTQPRSVSGSPGQSVTI SCTGTSSDVGGYKYVSWYQQ HPGKAPKLMIYDVSKRPSGV SNRFSGSKSGNTASLTISGL QAEDEADYYCSSYTSSSTYV FGTGTKVTVL SEQ ID NO. 37 |
| C4sh1A3 | QVQLVQSGAEVRKPGASVMV SCKASGYPFTSYAIHWLRQA PGQSLEWMGWIKPANGDITY SQKFQGRVTITGDISATTAY MELSSLRSEDTAMYYCAKGG GGYFDYWGQGTLVTVSS SEQ ID NO. 38 | SYVLTQPASVSGSPGQSITI SCTGTSSDVGNYNLVSWYQQ HPGKAPKLLVYDVSNRPSGV SNRFSGSKSGNTASLTISGL QAEDEADYYCSSYTTSSTYV FGIGTKVTVL SEQ ID NO. 39 |
| C4sh1A4 | QVQLVQSGAEVRKPGASVMV SCKASGYPFTSYAIHWLRQA PGQSLEWMGWIKPANGDITY SQKFQGRVTITGDISATTAY MELSSLRSEDTAMYYCAKGG GGYFDYWGQGTLVTVSS SEQ ID NO. 38 | QSVLTQPASMSGSPGQSITI SCTGTSSDVGTYDLVSWYQQ YPGKAPKLLIYDVANRPSGV SNRFSGSKSGNTASLTVSGL QAEDEADYYCSSYAGTKVYV FGTGTKVTVL SEQ ID NO. 40 |
| C4sh1A5 | EVQLVQSGAEVKKPGASVKV SCKASGYTFTGYYMHWVRQA PGQGLEWMGWINPNSGGTNY AQKFQGWVTMTRDTSISTAY MELSRLRSDDTAVYYCARDQ DFDYWGQGTLVTVSS SEQ ID NO. 41 | DVVMTQSPSSLSASVGDRVT ITCRASQGIATNLAWFQQKP GKAPKSLIYAASSLQSGVPS KFSGSGSGTAFTLTISSLQA EDFGTYYCQQYNNYPYTFGQ GTKVEIK SEQ ID NO. 42 |
| C4sh1A6 | QVQLVESGGGVVQPGRSLRL SCAASGFTFSTYAMHWVRQA PGRGLEWVAGISYDGSNKYH ADPVKGRFTISRDNSKNTLY LQMNNLRVEDSAVYYCAGDR SGGLDVWGQGTTVTVSS SEQ ID NO. 43 | DIVMTQSPSSLSASVGDRVT ITCRASQGISNSLAWYQQKS GKAPKLLLYAASGLESGVPS RFSGSGSGTDYTLTISSLQP EDFATYYCQQSYSMPLTFGG GTKVEIK SEQ ID NO. 44 |
| C4sh1A9 | QVQLVQSGAEVRKPGASVMV SCKASGYPFTSYAIHWLRQA PGQSLEWMGWIKPANGDITY SQKFQGRVTITGDISATTAY MELSSLRSEDTAMYYCAKGG GGYFDYWGQGTLVTVSS SEQ ID NO. 38 | QPVLTQPASVSGSPGQSITI SCTGTSSDVGGYNLVAWYQQ HPGKAPKLMIYDVSKRPSGV SNRFSGSKSGNTASLTISGL QAEDEADYYCSSYTSSSTSH YVFGTGTKVTVL SEQ ID NO. 45 |
| C4sh1B10 | EVQLVESGAEVKKPGASVKV SCKASGYTFTGYYMHWVRQA PGQGLEWMGWINPNSGGTNY AQKFQGRVTMTRDTSISTAY MELRSLRSDDTAVYYCARGG GAFDIWGQGTMVTVSS SEQ ID NO. 46 | QAVLTQPASVSGSPGQSITI SCTGTSSDVGSYNLVSWYQQ HPGKAPKLMIYEVRKRPSGV SNRFSASKSGNTASLTISGL QAEDEADYYCSSFTSSSTFV FGAGTKLTVL SEQ ID NO. 47 |
| C4sh1B11 | QVQLVQSGAEVKKPGASVKV SCKASGYTFTGYYMHWVRQA PGQGLEWMGWINPNSGGTNY AQKFQGWVTMTRDTSISTAY MELSSLRSDDTAVYYCARDQ DFDYWGQGTLVTVSS SEQ ID NO. 48 | SYVLTQPASVSGSPGQSITI SCTGTSSDVGGTNYVSWYQQ HPGKAPKLMIFDVSNRPSGV SNRFSGSKSGNTASLTISGL QAEDEADYYCSSYTSMRTLV FGGGTKLTVL SEQ ID NO. 49 |
| C4sh1B2 | QMQLVQSGAEVKKPGASVKV SCKASGYTFTGYYIHWVRQA PGQGLEWMGWINPNSGGTIY | QAGLTQPPSASGSPGQSVTI SCTGTSSDVGGYNSVSWYQQ HPGKAPKLMIYDVSNRPSGV |

Sequence Listing

| | Heavy chain variable domain region | Light chain variable domain region |
|---|---|---|
| | AQKFQGRVTMTRDTSISTAY MELSRLRSDDTAVYYCARGS TNFDSWGQGTLVTVSS SEQ ID NO. 50 | SNRFSGSKSGNTASLTISGL QAEDEADYYCSSYINSGTLV FGGGTKLTVL SEQ ID NO. 51 |
| C4sh1C10 | QVQLVQSGAEVRKPGASVMV SCKASGYPFTSYAIHWLRQA PGQSLEWMGWIKPANGDITY SQKFQGRVTITGDISATTAY MELSSLRSEDTAMYYCAKGG GGYFDYWGQGTLVTVSS SEQ ID NO. 38 | QSVLTQPASVSGSPGQSITI SCTGTSADVGHYNLVSWYQQ HPGKAPKLMIYDVTKRPSGV STRFSGSKSGNTASLTISGL QAEDESDYYCSSYTSSSTYV FGTGTKLTVL SEQ ID NO. 52 |
| C4sh1C5 | QVQLVESGAEVKKPGASVKV SCKASGYTFTSHYMHWRQA PGQGLEWMGVINPSGGSTSY AQKFQGRVTMTRDTSTSTVY MDLSSLRSEDTAVYYCARRS EAYYHGMDVWGQGTTVTVSS SEQ ID NO. 53 | NFMLTQPPSASGAPGQRVTI SCSGSTSNIGSNYVFWYQQL PGTAPKLLIYRNNQRPSGVP DRFSGSKSGTSASLAISGLQ SEDEADYYCAAWDDSLNGWV FGGGTKLTVL SEQ ID NO. 54 |
| C4sh1C6 | EVQLVQSGAEVKKPGASVKV SCKASGYTFTGYYMHWVRQA PGQGLEWMGWINPNSGGTNY AQKFQGWVTMTRDTSISTAY MELSRLRSDDTAVYYCARDQ DFDYWGQGTLVTVSS SEQ ID NO. 41 | EIVMTQSPSSLSASVGDRVT ITCRASRNIKTALAWFQQRP GQAPKSLIYAASSLHSGVTS RFSGSGFGTDFTLTINSLQP EDVATYYCQQYDSYPITFGQ GTRLEIK SEQ ID NO. 55 |
| C4sh1E10 | EVQLLESGAEVKKPGSSVKV SCKASGYPFTSYAIHWLRQA PGQSLEWMGWIKPANGDITY SQKFQGRVTITGDISATTAY MELSSLRSEDTAMYYCAKGG GGYFDYWGQGTLVTVSS SEQ ID NO. 56 | QAGLTQPASVSGSPGQWITI SCTGTSSDVGAYNLVSWYQQ YPGKAPKLMIYDVTKRPSGV SDRFSGSKSGNTASLTISGL QAEDEADYYCSSYTSSTTYV FGTGTQLTVL SEQ ID NO. 57 |
| C4sh1E12 | QVQLVQSGAEVRKPGASVMV SCKASGYPFTSYAIHWLRQA PGQSLEWMGWIKPANGDITY SQKFQGRVTITGDISATTAY MELSSLRSEDTAMYYCAKGG GGYFDYWGQGTLVTVSS SEQ ID NO. 38 | QPVLTQPRSVSGSPGQSVTI SCTGTSSDVGGYNLVSWYQQ HPGRAPKLMIYDVSDRPSGV SDRFSGSKSGNTASLTISGL QAEDEADYYCSSFTSRTTPA YVFGTGTKLTVL SEQ ID NO. 58 |
| C4sh1F11 | QVQLVQSGGGVVQPGRSLRL SCAASGFTFSSYAMHWVRQA PGKGLEWVAVISYDGTNKYY ADSVKGRFTISRDSSKNALY LQMNSLRTEDTALYYCARGG GWVVHAMDVWGQGTTVTVSS SEQ ID NO. 59 | QSVVTQPPSVSAAPGQKVTI SCSGSSSNIGNNYVSWYQQL PGTAPKLLIYDNNKRPSGIP DRFSGSKSGNTASLTISGLQ AEDEADYYCCSYAGSNTLIF GGGTKVTVL SEQ ID NO. 60 |
| C4sh1G4 | QVQLVQSGAEVRKPGASVMV SCKASGYPFTSYAIHWLRQA PGQSLEWMGWIKPANGDITY SQKFQGRVTITGDISATTAY MELSSLRSEDTAMYYCAKGG GGYFDYWGQGTLVTVSS SEQ ID NO. 38 | QSVLTQPASVSGSPGQSITI SCTGTSSDVGSYNLVSWYQQ HPGKAPKLMIYDVSERPSGV PDRFSGSKSGNTASLTISGL QAEDEADYYCSSYTSSSTLY VFGTGTKLTVL SEQ ID NO. 61 |
| C4sh1H9 | EVQLVQSGAEVKKPGASVKV SCKASGYTFTGYYMHWVRQA PGQGLEWMGWINPNSGGTNY AQKFQGWVTMTRDTSISTAY MELSRLRSDDTAVYYCARDQ DFDYWGQGTLVTVSS SEQ ID NO. 62 | QSVLTQPASVSGSPGQSITI SCTGTSSDVGGYNYVSWYQH HPDRAPKLMLYHVTQRPSGI SNRFSGSKSGNTASLTISGL QAEDEADYYCSSYTSTSTYV FGTGTKVTVL SEQ ID NO. 63 |

We claim:

1. An isolated anti-CD147 antibody, or an antigen binding fragment thereof, comprising a heavy chain variable domain and a light chain variable domain, comprising complementarity determining regions (CDRs) as set forth in
   a) a heavy chain variable domain comprising SEQ ID NO: 11, and a light chain variable domain comprising SEQ ID NO: 12;
   b) a heavy chain variable domain comprising SEQ ID NO: 41, and a light chain variable domain comprising SEQ ID NO: 42;
   c) a heavy chain variable domain comprising SEQ ID NO: 43, and a light chain variable domain comprising SEQ ID NO: 44; or
   d) a heavy chain variable domain comprising SEQ ID NO: 50, and a light chain variable domain comprising SEQ ID NO: 51.

2. The isolated fully human antibody of claim 1 comprising a heavy chain variable domain and a light chain variable domain, wherein the antibody comprises:
   a) a heavy chain variable domain comprising SEQ ID NO: 11, and a light chain variable domain comprising SEQ ID NO: 12;
   b) a heavy chain variable domain comprising SEQ ID NO: 41, and a light chain variable domain comprising SEQ ID NO: 42;
   c) a heavy chain variable domain comprising SEQ ID NO: 43, and a light chain variable domain comprising SEQ ID NO: 44: or
   d) a heavy chain variable domain comprising SEQ ID NO: 50, and a light chain variable domain comprising SEQ ID NO: 51.

3. The anti-CD147 antigen binding fragment of claim 1, wherein the antigen binding fragment is a Fab fragment comprising a heavy chain variable domain and a light chain variable domain, wherein the Fab fragment comprises:
   a) a heavy chain variable domain comprising SEQ ID NO: 11, and a light chain variable domain comprising SEQ ID NO: 12;
   b) a heavy chain variable domain comprising SEQ ID NO: 41, and a light chain variable domain comprising SEQ ID NO: 42;
   c) a heavy chain variable domain comprising SEQ ID NO: 43, and a light chain variable domain comprising SEQ ID NO: 44: or
   d) a heavy chain variable domain comprising SEQ ID NO: 50, and a light chain variable domain comprising SEQ ID NO: 51.

4. The anti-CD147 antigen binding fragment of claim 1, wherein the antigen binding fragment is a single chain human antibody comprising a heavy chain variable domain and a light chain variable domain, wherein a peptide linker connects the heavy chain and light chain variable domains and wherein the single chain human antibody comprises:
   a) a heavy chain variable domain comprising SEQ ID NO: 11, and a light chain variable domain comprising SEQ ID NO: 12;
   b) a heavy chain variable domain comprising SEQ ID NO: 41, and a light chain variable domain comprising SEQ ID NO: 42;
   c) a heavy chain variable domain comprising SEQ ID NO: 43, and a light chain variable domain comprising SEQ ID NO: 44; or
   d) a heavy chain variable domain comprising SEQ ID NO: 50, and a light chain variable domain comprising SEQ ID NO: 51.

5. A method of treating a subject having a CD147-expressing cancer or a non-oncology disease, comprising administering an effective amount of the isolated fully human antibody of claim 2 to the subject, wherein the non-oncology disease is selected from the group consisting of rheumatoid arthritis, experimental lung injury, atherosclerosis, chronic liver disease induced by hepatitis C virus, ischemic myocardial injury, and heart failure.

6. A method for treating a subject having a CD 147-expressing cancer or a non-oncology disease, comprising administering an effective amount of the anti-CD147 fully human antibody Fab fragment of claim 3 to the subject, wherein the non-oncology disease is selected from the group consisting of rheumatoid arthritis, experimental lung injury, atherosclerosis, chronic liver disease induced by hepatitis C virus, ischemic myocardial injury, and heart failure.

7. The method of claim 5, wherein the CD-147 expressing cancer is selected from the group consisting of prostate cancer, myeloid leukemia, hepatocellular carcinoma, squamous carcinoma, colon adenocarcinoma, lung carcinoma, and breast cancer.

8. The method of claim 6, wherein the CD-147 expressing cancer is selected from the group consisting of prostate cancer, myeloid leukemia, hepatocellular carcinoma, squamous carcinoma, colon adenocarcinoma, lung carcinoma, and breast cancer.

9. The antibody, or antigen-binding fragment thereof, of claim 1, which has a $K_D$ of at least $1 \times 10^{-6}$ M.

10. A method of treating a CD-147 expressing cancer comprising administering an effective amount of the anti-CD147 antibody of claim 1.

11. The method of claim 10, wherein the CD147 expressing cancer is selected from the group consisting of: prostate cancer, myeloid leukemia, hepatocellular carcinoma, squamous carcinoma, colon adenocarcinoma, lung carcinoma, and breast cancer.

12. A method of treating a non-oncology disease comprising administering an effective amount of the anti-CD 147 antibody of claim 1, wherein the non-oncology disease is selected from the group consisting of rheumatoid arthritis, experimental lung injury, atherosclerosis, chronic liver disease induced by hepatitis C virus, ischemic myocardial injury, and heart failure.

13. A pharmaceutical composition comprising the isolated fully human antibody of claim 2, and a pharmaceutically acceptable carrier.

14. A pharmaceutical composition comprising the anti-CD147 fully human antibody Fab fragment of claim 3, and a pharmaceutically acceptable carrier.

15. A pharmaceutical composition comprising the anti-CD147 antibody, or an antigen binding fragment thereof, of claim 1, and a pharmaceutically acceptable carrier.

* * * * *

```
                          SEQUENCE LISTING

<160> NUMBER OF SEQ ID NOS: 62

<210> SEQ ID NO 1
<211> LENGTH: 115
<212> TYPE: PRT
<213> ORGANISM: Homo sapiens

<400> SEQUENCE: 1

Val Gln Leu Val Gln Ser Gly Ala Glu Val Lys Lys Pro Gly Ala Ser
1               5                   10                  15

Val Lys Val Ser Cys Lys Ala Ser Gly Tyr Thr Phe Thr Gly Tyr Tyr
            20                  25                  30

Met His Trp Val Arg Gln Ala Pro Gly Gln Gly Leu Glu Trp Met Gly
        35                  40                  45

Trp Ile Asn Pro Asn Ser Gly Gly Thr Asn Tyr Ala Gln Lys Phe Gln
    50                  55                  60

Gly Arg Val Thr Met Thr Arg Asp Thr Ser Ala Ser Thr Ala Tyr Met
65                  70                  75                  80

Glu Leu Ser Gly Leu Arg Ser Glu Asp Thr Ala Val Tyr Tyr Cys Ala
                85                  90                  95

Arg Gly Asn Leu Phe Ile Asp Tyr Trp Gly Gln Gly Thr Leu Val Thr
            100                 105                 110

Val Ser Ser
        115
```

<210> SEQ ID NO 2
<211> LENGTH: 110
<212> TYPE: PRT
<213> ORGANISM: Homo sapiens

<400> SEQUENCE: 2

```
Leu Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Phe Val Phe Gly Gly Gly Thr Lys Leu Thr Val Leu
            100                 105                 110
```

<210> SEQ ID NO 3
<211> LENGTH: 118
<212> TYPE: PRT
<213> ORGANISM: Homo sapiens

<400> SEQUENCE: 3

```
Glu Val Gln Leu Val Glu Ser Gly Ala Glu Val Lys Lys Pro Gly Ala
1               5                   10                  15

Ser Val Arg Val Ser Cys Arg Ala Ser Gly Tyr Thr Phe Thr Asn Tyr
            20                  25                  30

Ala Ile Ser Trp Val Arg Gln Ala Pro Gly Gln Gly Leu Glu Trp Met
        35                  40                  45

Gly Trp Ile Ser Thr Tyr Asn Gly Asn Thr Leu Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Thr Asp Thr Tyr Tyr Phe Asp Tyr Trp Gly Gln Gly Thr
            100                 105                 110

Leu Val Thr Val Ser Ser
        115
```

<210> SEQ ID NO 4
<211> LENGTH: 110
<212> TYPE: PRT
<213> ORGANISM: Homo sapiens

<400> SEQUENCE: 4

```
Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Asp Lys Pro Pro Lys Leu
        35                  40                  45

Ile Ile Tyr Tyr Val Ser Asn Arg Pro Ser Gly Val Ser Asn Arg Phe
```

```
                    50                  55                  60
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Arg Ser Asn
                 85                  90                  95

Thr Asn Tyr Val Phe Gly Thr Gly Thr Lys Val Thr Val Leu
                100                 105                 110
```

<210> SEQ ID NO 5
<211> LENGTH: 120
<212> TYPE: PRT
<213> ORGANISM: Homo sapiens

<400> SEQUENCE: 5

```
Glu Val Gln Leu Leu Glu Ser Gly Ala Glu Val Lys Lys Pro Gly Ala
 1               5                  10                  15

Ser Val Lys Val Ser Cys Lys Ala Ser Gly Tyr Thr Phe Thr Ser His
                 20                  25                  30

Tyr Met His Trp Val Arg Gln Ala Pro Gly Gln Gly Leu Glu Trp Met
             35                  40                  45

Gly Val Ile Asn Pro Ser Gly Gly Ser Thr Ser Tyr Ala Gln Lys Phe
         50                  55                  60

Gln Gly Arg Val Thr Met Thr Arg Asp Thr Ser Thr Ser Thr Val Tyr
 65                  70                  75                  80

Met Asp Leu Ser Ser Leu Arg Ser Glu Asp Thr Ala Val Tyr Tyr Cys
                 85                  90                  95

Ala Arg Arg Ser Glu Ala Tyr Tyr His Gly Met Asp Val Trp Gly Gln
                100                 105                 110

Gly Thr Thr Val Thr Val Ser Ser
        115                 120
```

<210> SEQ ID NO 6
<211> LENGTH: 110
<212> TYPE: PRT
<213> ORGANISM: Homo sapiens

<400> SEQUENCE: 6

```
Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
                 20                  25                  30

Tyr Val Tyr Trp Tyr Gln Gln Phe Pro Gly Thr Thr Pro Lys Leu Leu
             35                  40                  45

Ile Tyr Arg Asn Asn Gln Arg Pro Ser Gly Val Pro Asp Arg Phe Ser
         50                  55                  60

Gly Ser Lys Ser Ala Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Trp Val Phe Gly Gly Gly Thr Lys Leu Thr Val Leu
                100                 105                 110
```

<210> SEQ ID NO 7
<211> LENGTH: 118
<212> TYPE: PRT
<213> ORGANISM: Homo sapiens

<400> SEQUENCE: 7

Glu Val Gln Leu Val Glu Ser Gly Ala Glu Val Lys Lys Pro Gly Ala
1               5                   10                  15

Ser Val Arg Val Ser Cys Arg Ala Ser Gly Tyr Thr Phe Thr Asn Tyr
            20                  25                  30

Ala Ile Ser Trp Val Arg Gln Ala Pro Gly Gln Gly Leu Glu Trp Met
        35                  40                  45

Gly Trp Ile Ser Thr Tyr Asn Gly Asn Thr Leu Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Thr Asp Thr Tyr Tyr Phe Asp Tyr Trp Gly Gln Gly Thr
            100                 105                 110

Leu Val Thr Val Ser Ser
        115

<210> SEQ ID NO 8
<211> LENGTH: 111
<212> TYPE: PRT
<213> ORGANISM: Homo sapiens

<400> SEQUENCE: 8

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asn Val Thr Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Gly
                85                  90                  95

Thr Thr Leu Ser Val Phe Gly Thr Gly Thr Lys Leu Thr Val Leu
            100                 105                 110

<210> SEQ ID NO 9
<211> LENGTH: 119
<212> TYPE: PRT
<213> ORGANISM: Homo sapiens

<400> SEQUENCE: 9

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

```
Ala Arg Gly Ala Thr Gly Gly Tyr Gly Met Asp Val Trp Gly Gln Gly
            100                 105                 110

Thr Thr Val Thr Val Ser Ser
        115
```

<210> SEQ ID NO 10
<211> LENGTH: 111
<212> TYPE: PRT
<213> ORGANISM: Homo sapiens

<400> SEQUENCE: 10

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Asn Asp Val Gly Ala Tyr
            20                  25                  30

Asn Tyr Val Ser Trp Tyr Gln Gln His Pro Ala Lys Ala Pro Lys Leu
        35                  40                  45

Met Ile Tyr Gly Val Thr Lys Arg Pro Ser Gly Val Pro Asp Arg Phe
    50                  55                  60

Ser Gly Ala Asn Ser Gly Asn Thr Ala Thr Leu Thr Ile Thr Arg Val
65                  70                  75                  80

Glu Ala Gly Asp Glu Ala Asp Tyr Phe Cys Gln Val Trp Glu Arg Ser
                85                  90                  95

Ser Gly Gln Tyr Val Phe Gly Thr Gly Thr Lys Leu Thr Val Leu
            100                 105                 110
```

<210> SEQ ID NO 11
<211> LENGTH: 120
<212> TYPE: PRT
<213> ORGANISM: Homo sapiens

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Gly Phe Thr Ser Tyr
            20                  25                  30

Ala Ile His Trp Leu Arg Gln Ala Pro Gly Gln Arg Leu Glu Trp Met
        35                  40                  45

Gly Trp Ile Asn Pro Gly Asn Gly Asn Thr Lys Tyr Ser Gln Lys Phe
    50                  55                  60

Gln Gly Arg Val Thr Ile Thr Arg Asp Thr Ser Ala Thr Thr Ala Tyr
65                  70                  75                  80

Met Glu Leu Thr Ser Leu Arg Ser Glu Asp Ser Asp Thr Ala Val Tyr
                85                  90                  95

Tyr Cys Ala Arg Asp Leu Asp Gly Gly Ser Phe Asp His Trp Gly Gln
            100                 105                 110

Gly Thr Leu Val Thr Val Ser Ser
        115                 120
```

<210> SEQ ID NO 12
<211> LENGTH: 110
<212> TYPE: PRT
<213> ORGANISM: Homo sapiens

<400> SEQUENCE: 12

```
Gln Ser Val Val Thr Gln Pro Ala Ser Val Ser Gly Ser Pro Gly Gln
1               5                   10                  15
```

-continued

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
            35                  40                  45

Met Ile Tyr Asp Val Thr Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Arg Ser
            85                  90                  95

Ser Thr Tyr Val Phe Gly Thr Gly Thr Lys Val Thr Val Leu
        100                 105                 110

<210> SEQ ID NO 13
<211> LENGTH: 119
<212> TYPE: PRT
<213> ORGANISM: Homo sapiens

<400> SEQUENCE: 13

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Thr Tyr
            20                  25                  30

Trp Ile His Trp Val Arg Gln Ala Pro Gly Gln Gly Pro Glu Trp Met
        35                  40                  45

Gly Leu Ile Lys Pro Ser Ser Gly Ser Thr Thr Tyr Pro Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Leu Glu Gly Ile Gly Ala Ala Ser Asn Asp Trp Gly Gln Gly
        100                 105                 110

Thr Leu Val Thr Val Ser Ser
        115

<210> SEQ ID NO 14
<211> LENGTH: 109
<212> TYPE: PRT
<213> ORGANISM: Homo sapiens

<400> SEQUENCE: 14

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
            85                  90                  95

Ala Arg Val Phe Gly Thr Gly Thr Lys Val Thr Val Leu
        100                 105

<210> SEQ ID NO 15
<211> LENGTH: 119
<212> TYPE: PRT
<213> ORGANISM: Homo sapiens

<400> SEQUENCE: 15

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Thr Tyr
            20                  25                  30

Trp Ile His Trp Val Arg Gln Ala Pro Gly Gln Gly Pro Glu Trp Met
        35                  40                  45

Gly Leu Ile Lys Pro Ser Ser Gly Ser Thr Thr Tyr Pro Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Glu Gly Ile Gly Ala Ala Ser Asn Asp Trp Gly Gln Gly
            100                 105                 110

Thr Leu Val Thr Val Ser Ser
        115

<210> SEQ ID NO 16
<211> LENGTH: 109
<212> TYPE: PRT
<213> ORGANISM: Homo sapiens

<400> SEQUENCE: 16

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Asp Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
    50                  55                  60

Ser Ala Ser Leu Leu Gly Gly Lys Ala Ala Leu Thr Leu Ser Gly Ala
65                  70                  75                  80

Gln Pro Glu Asp Glu Ala Asp Tyr Tyr Cys Leu Leu Ala Tyr Ser Glu
                85                  90                  95

Val Arg Val Phe Gly Gly Gly Thr Gln Leu Thr Val Leu
            100                 105

<210> SEQ ID NO 17
<211> LENGTH: 124
<212> TYPE: PRT
<213> ORGANISM: Homo sapiens

<400> SEQUENCE: 17

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Arg Ser Tyr
            20                  25                  30

Asp Ile Asn Trp Val Arg Gln Ala Pro Gly Gln Gly Leu Glu Trp Met
        35                  40                  45

Gly Phe Leu Asn Pro Ser Asp Gly Gly Thr Thr Tyr Ala Gln Lys Phe

```
                    50                  55                  60
Gln Gly Arg Val Thr Val Thr Ser Asp Thr Ser Thr Ser Thr Val Tyr
 65                  70                  75                  80

Met Glu Leu Ser Ser Leu Arg Ser Glu Asn Thr Ala Val Tyr Tyr Cys
                     85                  90                  95

Ala Arg Val Gly Ile Thr Ser Thr Glu Thr Arg Ala Glu Tyr Phe Gln
                100                 105                 110

His Trp Gly Gln Gly Thr Leu Val Thr Val Ser Ser
                115                 120
```

<210> SEQ ID NO 18
<211> LENGTH: 110
<212> TYPE: PRT
<213> ORGANISM: Homo sapiens

<400> SEQUENCE: 18

```
Gln Ser Val Leu Thr Gln Pro Pro Ser Ala Ser Gly Ser Pro Gly Gln
  1               5                  10                  15

Ser Val Thr Ile Ser Cys Thr Gly Ser Ala Ser Asp Ile Gly His Ser
                 20                  25                  30

Phe Tyr Val Ser Trp Tyr Arg Gln Tyr Pro Gly Lys Ala Pro Asp Leu
             35                  40                  45

Leu Ile Phe Gln Val Asn Gln Arg Pro Ser Gly Val Pro Asn Arg Phe
 50                  55                  60

Ser Ala Ser Lys Ser Gly Asn Thr Ala Ser Leu Thr Val Ser Gly Leu
 65                  70                  75                  80

Gln Ile Glu Asp Glu Ala Asp Tyr Tyr Cys Ser Ser Tyr Ala Gly Gly
                 85                  90                  95

Thr Ser Ile Val Phe Gly Ser Gly Thr Lys Leu Thr Val Leu
                100                 105                 110
```

<210> SEQ ID NO 19
<211> LENGTH: 118
<212> TYPE: PRT
<213> ORGANISM: Homo sapiens

<400> SEQUENCE: 19

```
Gln Val Gln Leu Val Gln Ser Gly Ala Glu Val Lys Lys Pro Gly Ala
  1               5                  10                  15

Ser Val Lys Leu Ser Cys Lys Ala Ser Gly Tyr Thr Phe Thr Arg Tyr
                 20                  25                  30

Trp Val His Trp Val Arg Gln Ala Pro Gly Gln Gly Pro Glu Trp Met
             35                  40                  45

Gly Leu Ile Lys Pro Arg Asp Gly Ala Thr Thr Tyr Ala Gln Lys Phe
 50                  55                  60

Gln Gly Arg Val Thr Leu Thr Arg Asp Thr Ser Thr Thr Thr Val Tyr
 65                  70                  75                  80

Met Glu Leu Thr Ser Leu Arg Ser Glu Asp Thr Gly Ile Tyr Tyr Cys
                 85                  90                  95

Gly Leu Leu Glu Gly Asp Asp Ala Phe Asp Val Trp Gly Gln Gly Thr
                100                 105                 110

Met Val Thr Val Ser Ser
                115
```

<210> SEQ ID NO 20
<211> LENGTH: 109
<212> TYPE: PRT

<213> ORGANISM: Homo sapiens

<400> SEQUENCE: 20

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Pro Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Ala Arg Val Phe Gly Gly Gly Thr Lys Leu Thr Val Leu
            100                 105
```

<210> SEQ ID NO 21
<211> LENGTH: 119
<212> TYPE: PRT
<213> ORGANISM: Homo sapiens

<400> SEQUENCE: 21

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Tyr Gly Ser Gly Ser Leu Asp Tyr Trp Gly Gln Gly
            100                 105                 110

Thr Leu Val Thr Val Ser Ser
        115
```

<210> SEQ ID NO 22
<211> LENGTH: 108
<212> TYPE: PRT
<213> ORGANISM: Homo sapiens

<400> SEQUENCE: 22

```
Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Arg Ser Asn Trp Pro Gln
                85                  90                  95

Ile Thr Phe Gly Gln Gly Thr Arg Leu Glu Ile Lys
            100                 105

<210> SEQ ID NO 23
<211> LENGTH: 125
<212> TYPE: PRT
<213> ORGANISM: Homo sapiens

<400> SEQUENCE: 23

Gln Val Gln Leu Val Gln Ser Gly Gly Val Val Arg Pro Gly Gly
1               5                   10                  15

Ser Leu Arg Leu Ser Cys Ala Ala Ser Gly Phe Thr Phe Gly Asp Tyr
                20                  25                  30

Gly Met Ser Trp Val Arg Gln Ala Pro Gly Arg Gly Leu Glu Trp Val
            35                  40                  45

Ala Gly Ile Ile Trp Asn Gly Gly Thr Thr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Glu Met Asn Ser Leu Arg Ala Glu Asp Thr Ala Val Tyr Tyr Cys
                85                  90                  95

Thr Arg Asp Leu Asn Tyr Tyr Ile Ser Gly Tyr Tyr Asp Ala Phe
                100                 105                 110

Asp Ile Trp Gly Gln Gly Thr Met Val Thr Val Ser Ser
            115                 120                 125

<210> SEQ ID NO 24
<211> LENGTH: 108
<212> TYPE: PRT
<213> ORGANISM: Homo sapiens

<400> SEQUENCE: 24

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Arg Val Phe Gly Gly Gly Thr Lys Leu Thr Val Leu
            100                 105

<210> SEQ ID NO 25
<211> LENGTH: 109
<212> TYPE: PRT
<213> ORGANISM: Homo sapiens

<400> SEQUENCE: 25

Gln Thr Val Val Thr Gln Glu Pro Ser Leu Thr Val Ser Pro Gly Gly
1               5                   10                  15

Thr Val Thr Leu Thr Cys Gly Ser Asp Thr Gly Ala Val Asn Ser Gly
            20                  25                  30

His Tyr Pro Tyr Trp Phe Gln Gln Lys Pro Gly Gln Ala Pro Arg Ala
        35                  40                  45

Leu Ile Tyr Asp Thr Gly Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Thr Arg Ile Phe Gly Gly Gly Thr Lys Leu Thr Val Leu
            100                 105

<210> SEQ ID NO 26
<211> LENGTH: 122
<212> TYPE: PRT
<213> ORGANISM: Homo sapiens

<400> SEQUENCE: 26

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Lys Gly His Ser Gly Gly Trp Tyr Ala Phe Asp Ile Trp
            100                 105                 110

Gly Gln Gly Thr Met Val Thr Val Ser Ser
        115                 120

<210> SEQ ID NO 27
<211> LENGTH: 110
<212> TYPE: PRT
<213> ORGANISM: Homo sapiens

<400> SEQUENCE: 27

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Arg Arg
            20                  25                  30

Ala Val Asn Trp Tyr Gln Gln Leu Pro Gly Thr Ala Pro Lys Leu Leu
        35                  40                  45

Ile Tyr Asp Asn Asp Arg Arg Pro Ser Gly Ile Pro Asp Arg Phe Ser
    50                  55                  60

Gly Ser Lys Ser Gly Thr Ser Ala Thr Leu Gly Ile Thr Glu Leu Gln
65                  70                  75                  80

Thr Gly Asp Glu Ala Asp Tyr Tyr Cys Gly Thr Trp Asp Thr Asn Leu
                85                  90                  95

Ser Ala Gly Leu Phe Gly Gly Gly Thr Lys Leu Thr Val Leu
            100                 105                 110

<210> SEQ ID NO 28
<211> LENGTH: 119
<212> TYPE: PRT
<213> ORGANISM: Homo sapiens

<400> SEQUENCE: 28

Gln Val Gln Leu Gln Gln Ser Gly Pro Gly Leu Val Lys Pro Ala Gln
1               5                   10                  15

Thr Leu Ser Leu Thr Cys Ala Ile Ser Gly Asp Ser Val Ser Ser
            20                  25                  30

Arg Ala Ala Trp Asn Trp Ile Arg Gln Ser Pro Ser Arg Gly Leu Glu
        35                  40                  45

Trp Leu Gly Arg Thr Phe Tyr Arg Ser Arg Trp Asn Asn Glu Tyr Ala
    50                  55                  60

Glu Thr Val Lys Ser Arg Ile Thr Ile Asn Pro Asp Thr Ser Thr Asn
65                  70                  75                  80

His Phe Ser Leu Gln Leu Thr Ser Val Ser Pro Glu Asp Thr Ala Ile
                85                  90                  95

Tyr Tyr Cys Ala Arg Gly Gly Gly Asn Phe Asp Ser Trp Gly Gln Gly
            100                 105                 110

Thr Leu Val Thr Val Ser Ser
        115

<210> SEQ ID NO 29
<211> LENGTH: 90
<212> TYPE: PRT
<213> ORGANISM: Homo sapiens

<400> SEQUENCE: 29

Ser Gly Ser Ser Ser Asn Ile Gly Asn Asn Tyr Val Ser Trp Tyr Gln
1               5                   10                  15

Gln Leu Pro Gly Thr Ala Pro Lys Leu Leu Ile Tyr Asp Asn Asn Lys
            20                  25                  30

Arg Pro Ser Gly Ile Pro Asp Arg Phe Ser Gly Ser Lys Ser Gly Thr
        35                  40                  45

Ser Ala Thr Leu Gly Ile Thr Gly Leu Gln Thr Gly Asp Glu Ala Asp
    50                  55                  60

Tyr Tyr Cys Gly Thr Trp Asp Ser Ser Leu Ser Ala Gly Asp Val Val
65                  70                  75                  80

Phe Gly Gly Gly Thr Lys Leu Thr Val Leu
                85                  90

<210> SEQ ID NO 30
<211> LENGTH: 119
<212> TYPE: PRT
<213> ORGANISM: Homo sapiens

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr

```
                    65                  70                  75                  80
Met Glu Leu Ser Ser Leu Arg Ser Glu Asp Thr Ala Val Tyr Tyr Cys
                    85                  90                  95

Ala Arg Glu Ser Glu Asp Ser Ile Ala Phe Asp Ile Trp Gly Gln Gly
                100                 105                 110

Thr Met Val Thr Val Ser Ser
            115

<210> SEQ ID NO 31
<211> LENGTH: 109
<212> TYPE: PRT
<213> ORGANISM: Homo sapiens

<400> SEQUENCE: 31

Ala Ile Gln Leu Thr Gln Ser Pro Gly Thr Leu Ser Leu Ala Pro Gly
1               5                   10                  15

Glu Arg Ala Thr Leu Ser Cys Arg Ala Ser Gln Ser Val Ser Ser Ser
                20                  25                  30

Tyr Ile Ala Trp Tyr Gln Gln Arg Pro Gly Gln Ala Pro Arg Leu Leu
            35                  40                  45

Ile Tyr Gly Ala Ser Asn Arg Ala Thr Asp Ile Pro Ala Arg Phe Ile
        50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Arg Ser Asn Trp Pro
                85                  90                  95

Arg Asn Thr Phe Gly Gln Gly Thr Arg Leu Glu Ile Lys
                100                 105

<210> SEQ ID NO 32
<211> LENGTH: 109
<212> TYPE: PRT
<213> ORGANISM: Homo sapiens

<400> SEQUENCE: 32

Gln Thr Val Val Thr Gln Glu Pro Ser Leu Thr Val Ser Pro Gly Gly
1               5                   10                  15

Thr Val Thr Leu Thr Cys Gly Ser Asn Thr Gly Ala Val Thr Ser Gly
                20                  25                  30

His Tyr Pro Tyr Trp Phe Gln Gln Lys Pro Gly Gln Ala Pro Arg Thr
            35                  40                  45

Leu Ile Tyr Asp Ala Thr Asn Lys Gln Ser Trp Thr Pro Ala Arg Phe
        50                  55                  60

Ser Gly Ser Leu Leu Gly Asp Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Val Arg Val Phe Gly Gly Gly Thr Lys Leu Thr Val Leu
                100                 105

<210> SEQ ID NO 33
<211> LENGTH: 109
<212> TYPE: PRT
<213> ORGANISM: Homo sapiens

<400> SEQUENCE: 33

Gln Thr Val Val Thr Gln Glu Pro Ser Leu Thr Val Ser Pro Gly Gly
1               5                   10                  15
```

```
Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
            35                  40                  45

Leu Ile Tyr Asp Thr Ser Asn Lys His Ser Trp Thr Pro Ala Arg Phe
 50                      55                  60

Ser Gly Ser Leu Leu Gly Gly Lys Ala Ala Leu Thr Leu Ser Gly Ala
 65                  70                  75                  80

Gln Pro Glu Asp Glu Ala Asp Tyr Phe Cys Leu Leu Ser Ser Ser Gly
                85                  90                  95

Ala Arg Val Phe Gly Gly Gly Thr Lys Leu Thr Val Leu
            100                 105
```

<210> SEQ ID NO 34
<211> LENGTH: 117
<212> TYPE: PRT
<213> ORGANISM: Homo sapiens

<400> SEQUENCE: 34

```
Gln Val Gln Leu Val Gln Ser Gly Ala Glu Val Arg Lys Pro Gly Ala
 1               5                   10                  15

Ser Val Met Val Ser Cys Lys Ala Ser Gly Tyr Pro Phe Thr Ser Tyr
            20                  25                  30

Ala Ile His Trp Leu Arg Gln Ala Pro Gly Gln Ser Leu Glu Trp Met
            35                  40                  45

Gly Trp Ile Lys Pro Ala Asn Gly Asp Ile Thr Tyr Ser Gln Lys Phe
 50                      55                  60

Gln Gly Arg Val Thr Ile Thr Gly Asp Ile Ser Ala Thr Thr Ala Tyr
 65                  70                  75                  80

Met Glu Leu Ser Ser Leu Arg Ser Glu Asp Thr Ala Met Tyr Tyr Cys
                85                  90                  95

Thr Lys Gly Gly Gly Gly Tyr Phe Asp Tyr Trp Gly Gln Gly Thr Leu
            100                 105                 110

Val Thr Val Ser Ser
        115
```

<210> SEQ ID NO 35
<211> LENGTH: 110
<212> TYPE: PRT
<213> ORGANISM: Homo sapiens

<400> SEQUENCE: 35

```
Gln Ser Val Leu Thr Gln Pro Arg Ser Val Ser Gly Ser Pro Gly Gln
 1               5                   10                  15

Ser Val Thr Ile Ser Cys Thr Gly Thr Ser Ser Asp Val Gly Gly Tyr
            20                  25                  30

Asn Leu Val Ser Trp Tyr Gln Gln His Pro Gly Lys Ala Pro Lys Leu
            35                  40                  45

Met Ile Tyr Asp Val His Lys Arg Pro Ser Gly Thr Ser Thr Arg Phe
 50                      55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Arg Ser Gly
                85                  90                  95

Ser Thr Tyr Val Phe Gly Thr Gly Thr Lys Val Thr Val Leu
            100                 105                 110
```

<210> SEQ ID NO 36
<211> LENGTH: 118
<212> TYPE: PRT
<213> ORGANISM: Homo sapiens

<400> SEQUENCE: 36

Gln Val Gln Leu Val Gln Ser Gly Ala Glu Val Lys Lys Pro Gly Glu
1               5                   10                  15

Ser Leu Arg Ile Ser Cys Gln Gly Ser Gly Tyr Ser Phe Ile Asn His
            20                  25                  30

Trp Ile Ser Trp Val Arg Gln Met Pro Gly Lys Gly Leu Glu Trp Leu
        35                  40                  45

Gly Arg Ile Asp Pro Ser Asp Ser Tyr Thr Asn Tyr Ser Pro Ser Val
    50                  55                  60

Gln Gly His Val Thr Ile Ser Val Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg His Asp Arg Asn Val Tyr Phe Asp Pro Trp Gly Gln Gly Thr
            100                 105                 110

Leu Val Thr Val Ser Ser
        115

<210> SEQ ID NO 37
<211> LENGTH: 110
<212> TYPE: PRT
<213> ORGANISM: Homo sapiens

<400> SEQUENCE: 37

Ser Tyr Glu Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Lys Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Val Thr Val Leu
            100                 105                 110

<210> SEQ ID NO 38
<211> LENGTH: 117
<212> TYPE: PRT
<213> ORGANISM: Homo sapiens

<400> SEQUENCE: 38

Gln Val Gln Leu Val Gln Ser Gly Ala Glu Val Arg Lys Pro Gly Ala
1               5                   10                  15

Ser Val Met Val Ser Cys Lys Ala Ser Gly Tyr Pro Phe Thr Ser Tyr
            20                  25                  30

Ala Ile His Trp Leu Arg Gln Ala Pro Gly Gln Ser Leu Glu Trp Met
        35                  40                  45

Gly Trp Ile Lys Pro Ala Asn Gly Asp Ile Thr Tyr Ser Gln Lys Phe
            50                  55                  60

Gln Gly Arg Val Thr Ile Thr Gly Asp Ile Ser Ala Thr Thr Ala Tyr
65                  70                  75                  80

Met Glu Leu Ser Ser Leu Arg Ser Glu Asp Thr Ala Met Tyr Tyr Cys
                85                  90                  95

Ala Lys Gly Gly Gly Tyr Phe Asp Tyr Trp Gly Gln Gly Thr Leu
            100                 105                 110

Val Thr Val Ser Ser
            115

<210> SEQ ID NO 39
<211> LENGTH: 110
<212> TYPE: PRT
<213> ORGANISM: Homo sapiens

<400> SEQUENCE: 39

Ser Tyr Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asn Tyr
            20                  25                  30

Asn Leu Val Ser Trp Tyr Gln Gln His Pro Gly Lys Ala Pro Lys Leu
        35                  40                  45

Leu Val Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Ser Thr Tyr Val Phe Gly Ile Gly Thr Lys Val Thr Val Leu
            100                 105                 110

<210> SEQ ID NO 40
<211> LENGTH: 115
<212> TYPE: PRT
<213> ORGANISM: Homo sapiens

<400> SEQUENCE: 40

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gln Asp Phe Asp Tyr Trp Gly Gln Gly Thr Leu Val Thr
            100                 105                 110

Val Ser Ser
            115

<210> SEQ ID NO 41
<211> LENGTH: 107

<212> TYPE: PRT
<213> ORGANISM: Homo sapiens

<400> SEQUENCE: 41

Asp Val Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ala Thr Asn
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Ala Phe Thr Leu Thr Ile Ser Ser Leu Gln Ala
65                  70                  75                  80

Glu Asp Phe Gly Thr Tyr Tyr Cys Gln Gln Tyr Asn Asn Tyr Pro Tyr
                85                  90                  95

Thr Phe Gly Gln Gly Thr Lys Val Glu Ile Lys
            100                 105

<210> SEQ ID NO 42
<211> LENGTH: 117
<212> TYPE: PRT
<213> ORGANISM: Homo sapiens

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Arg Gly Leu Glu Trp Val
        35                  40                  45

Ala Gly Ile Ser Tyr Asp Gly Ser Asn Lys Tyr His Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Val Glu Asp Ser Ala Val Tyr Tyr Cys
                85                  90                  95

Ala Gly Asp Arg Ser Gly Gly Leu Asp Val Trp Gly Gln Gly Thr Thr
            100                 105                 110

Val Thr Val Ser Ser
        115

<210> SEQ ID NO 43
<211> LENGTH: 107
<212> TYPE: PRT
<213> ORGANISM: Homo sapiens

<400> SEQUENCE: 43

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Ser Gly Lys Ala Pro Lys Leu Leu Leu
        35                  40                  45

Tyr Ala Ala Ser Gly Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro

```
                65                  70                  75                  80
Glu Asp Phe Ala Thr Tyr Tyr Cys Gln Gln Ser Tyr Ser Met Pro Leu
                    85                  90                  95

Thr Phe Gly Gly Gly Thr Lys Val Glu Ile Lys
                    100                 105
```

<210> SEQ ID NO 44
<211> LENGTH: 112
<212> TYPE: PRT
<213> ORGANISM: Homo sapiens

<400> SEQUENCE: 44

```
Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Leu Val Ala Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Ser His Tyr Val Phe Gly Thr Gly Thr Lys Val Thr Val Leu
                100                 105                 110
```

<210> SEQ ID NO 45
<211> LENGTH: 116
<212> TYPE: PRT
<213> ORGANISM: Homo sapiens

<400> SEQUENCE: 45

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Ala Phe Asp Ile Trp Gly Gln Gly Thr Met Val
                100                 105                 110

Thr Val Ser Ser
            115
```

<210> SEQ ID NO 46
<211> LENGTH: 110
<212> TYPE: PRT
<213> ORGANISM: Homo sapiens

<400> SEQUENCE: 46

```
Gln Ala Val Leu Thr Gln Pro Ala Ser Val Ser Gly Ser Pro Gly Gln
1               5                   10                  15
```

```
Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Arg Lys Arg Pro Ser Gly Val Ser Asn Arg Phe
    50                  55                  60

Ser Ala Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Ser Ser
                85                  90                  95

Ser Thr Phe Val Phe Gly Ala Gly Thr Lys Leu Thr Val Leu
            100                 105                 110
```

<210> SEQ ID NO 47
<211> LENGTH: 115
<212> TYPE: PRT
<213> ORGANISM: Homo sapiens

<400> SEQUENCE: 47

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gln Asp Phe Asp Tyr Trp Gly Gln Gly Thr Leu Val Thr
            100                 105                 110

Val Ser Ser
        115
```

<210> SEQ ID NO 48
<211> LENGTH: 110
<212> TYPE: PRT
<213> ORGANISM: Homo sapiens

<400> SEQUENCE: 48

```
Ser Tyr Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Thr
            20                  25                  30

Asn Tyr Val Ser Trp Tyr Gln Gln His Pro Gly Lys Ala Pro Lys Leu
        35                  40                  45

Met Ile Phe Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Met
                85                  90                  95

Arg Thr Leu Val Phe Gly Gly Gly Thr Lys Leu Thr Val Leu
            100                 105                 110
```

<210> SEQ ID NO 49
<211> LENGTH: 116
<212> TYPE: PRT
<213> ORGANISM: Homo sapiens

<400> SEQUENCE: 49

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Ile His Trp Val Arg Gln Ala Pro Gly Gln Gly Leu Glu Trp Met
            35                  40                  45

Gly Trp Ile Asn Pro Asn Ser Gly Gly Thr Ile Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ser Thr Asn Phe Asp Ser Trp Gly Gln Gly Thr Leu Val
            100                 105                 110

Thr Val Ser Ser
        115

<210> SEQ ID NO 50
<211> LENGTH: 110
<212> TYPE: PRT
<213> ORGANISM: Homo sapiens

<400> SEQUENCE: 50

Gln Ala Gly Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ile Asn Ser
                85                  90                  95

Gly Thr Leu Val Phe Gly Gly Gly Thr Lys Leu Thr Val Leu
            100                 105                 110

<210> SEQ ID NO 51
<211> LENGTH: 110
<212> TYPE: PRT
<213> ORGANISM: Homo sapiens

<400> SEQUENCE: 51

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ala Asp Val Gly His Tyr
                20                  25                  30

Asn Leu Val Ser Trp Tyr Gln Gln His Pro Gly Lys Ala Pro Lys Leu
            35                  40                  45

```
Met Ile Tyr Asp Val Thr Lys Arg Pro Ser Gly Val Ser Thr Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ser Asp Tyr Tyr Cys Ser Ser Tyr Thr Ser Ser
                 85                  90                  95

Ser Thr Tyr Val Phe Gly Thr Gly Thr Lys Leu Thr Val Leu
            100                 105                 110

<210> SEQ ID NO 52
<211> LENGTH: 120
<212> TYPE: PRT
<213> ORGANISM: Homo sapiens

<400> SEQUENCE: 52

Gln Val Gln Leu Val Glu Ser Gly Ala Glu Val Lys Lys Pro Gly Ala
1               5                  10                  15

Ser Val Lys Val Ser Cys Lys Ala Ser Gly Tyr Thr Phe Thr Ser His
            20                  25                  30

Tyr Met His Trp Val Arg Gln Ala Pro Gly Gln Gly Leu Glu Trp Met
         35                  40                  45

Gly Val Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Asp Leu Ser Ser Leu Arg Ser Glu Asp Thr Ala Val Tyr Tyr Cys
                 85                  90                  95

Ala Arg Arg Ser Glu Ala Tyr Tyr His Gly Met Asp Val Trp Gly Gln
            100                 105                 110

Gly Thr Thr Val Thr Val Ser Ser
         115                 120

<210> SEQ ID NO 53
<211> LENGTH: 110
<212> TYPE: PRT
<213> ORGANISM: Homo sapiens

<400> SEQUENCE: 53

Asn Phe Met Leu Thr Gln Pro Pro Ser Ala Ser Gly Ala Pro Gly Gln
1               5                  10                  15

Arg Val Thr Ile Ser Cys Ser Gly Ser Thr Ser Asn Ile Gly Ser Asn
            20                  25                  30

Tyr Val Phe Trp Tyr Gln Gln Leu Pro Gly Thr Ala Pro Lys Leu Leu
         35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Trp Val Phe Gly Gly Gly Thr Lys Leu Thr Val Leu
            100                 105                 110

<210> SEQ ID NO 54
<211> LENGTH: 107
<212> TYPE: PRT
<213> ORGANISM: Homo sapiens
```

```
<400> SEQUENCE: 54

Glu Ile Val Met Thr Gln Ser Pro Ser Ser Leu Ser Ala Ser Val Gly
1               5                   10                  15

Asp Arg Val Thr Ile Thr Cys Arg Ala Ser Arg Asn Ile Lys Thr Ala
            20                  25                  30

Leu Ala Trp Phe Gln Gln Arg Pro Gly Gln Ala Pro Lys Ser Leu Ile
        35                  40                  45

Tyr Ala Ala Ser Ser Leu His Ser Gly Val Thr Ser Arg Phe Ser Gly
50                  55                  60

Ser Gly Phe Gly Thr Asp Phe Thr Leu Thr Ile Asn Ser Leu Gln Pro
65                  70                  75                  80

Glu Asp Val Ala Thr Tyr Tyr Cys Gln Gln Tyr Asp Ser Tyr Pro Ile
                85                  90                  95

Thr Phe Gly Gln Gly Thr Arg Leu Glu Ile Lys
            100                 105

<210> SEQ ID NO 55
<211> LENGTH: 117
<212> TYPE: PRT
<213> ORGANISM: Homo sapiens

<400> SEQUENCE: 55

Glu Val Gln Leu Leu Glu Ser Gly Ala Glu Val Lys Lys Pro Gly Ser
1               5                   10                  15

Ser Val Lys Val Ser Cys Lys Ala Ser Gly Tyr Pro Phe Thr Ser Tyr
            20                  25                  30

Ala Ile His Trp Leu Arg Gln Ala Pro Gly Gln Ser Leu Glu Trp Met
        35                  40                  45

Gly Trp Ile Lys Pro Ala Asn Gly Asp Ile Thr Tyr Ser Gln Lys Phe
50                  55                  60

Gln Gly Arg Val Thr Ile Thr Gly Asp Ile Ser Ala Thr Thr Ala Tyr
65                  70                  75                  80

Met Glu Leu Ser Ser Leu Arg Ser Glu Asp Thr Ala Met Tyr Tyr Cys
                85                  90                  95

Ala Lys Gly Gly Gly Tyr Phe Asp Tyr Trp Gly Gln Gly Thr Leu
            100                 105                 110

Val Thr Val Ser Ser
        115

<210> SEQ ID NO 56
<211> LENGTH: 110
<212> TYPE: PRT
<213> ORGANISM: Homo sapiens

<400> SEQUENCE: 56

Gln Ala Gly Leu Thr Gln Pro Ala Ser Val Ser Gly Ser Pro Gly Gln
1               5                   10                  15

Trp Ile Thr Ile Ser Cys Thr Gly Thr Ser Ser Asp Val Gly Ala Tyr
            20                  25                  30

Asn Leu Val Ser Trp Tyr Gln Gln Tyr Pro Gly Lys Ala Pro Lys Leu
        35                  40                  45

Met Ile Tyr Asp Val Thr Lys Arg Pro Ser Gly Val Ser Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
```

```
                     85                  90                  95

Thr Thr Tyr Val Phe Gly Thr Gly Thr Gln Leu Thr Val Leu
                100                 105                 110

<210> SEQ ID NO 57
<211> LENGTH: 112
<212> TYPE: PRT
<213> ORGANISM: Homo sapiens

<400> SEQUENCE: 57

Gln Pro Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Leu Val Ser Trp Tyr Gln Gln His Pro Gly Arg Ala Pro Lys Leu
            35                  40                  45

Met Ile Tyr Asp Val Ser Asp Arg Pro Ser Gly Val Ser Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Ser Arg
                85                  90                  95

Thr Thr Pro Ala Tyr Val Phe Gly Thr Gly Thr Lys Leu Thr Val Leu
                100                 105                 110

<210> SEQ ID NO 58
<211> LENGTH: 120
<212> TYPE: PRT
<213> ORGANISM: Homo sapiens

<400> SEQUENCE: 58

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Thr Asn Lys Tyr Tyr Ala Asp Ser Val
        50                  55                  60

Lys Gly Arg Phe Thr Ile Ser Arg Asp Ser Ser Lys Asn Ala Leu Tyr
65                  70                  75                  80

Leu Gln Met Asn Ser Leu Arg Thr Glu Asp Thr Ala Leu Tyr Tyr Cys
                85                  90                  95

Ala Arg Gly Gly Gly Trp Val Val His Ala Met Asp Val Trp Gly Gln
                100                 105                 110

Gly Thr Thr Val Thr Val Ser Ser
            115                 120

<210> SEQ ID NO 59
<211> LENGTH: 109
<212> TYPE: PRT
<213> ORGANISM: Homo sapiens

<400> SEQUENCE: 59

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30
```

```
Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Cys Ser Tyr Ala Gly Ser Asn
                85                  90                  95

Thr Leu Ile Phe Gly Gly Gly Thr Lys Val Thr Val Leu
                100                 105

<210> SEQ ID NO 60
<211> LENGTH: 111
<212> TYPE: PRT
<213> ORGANISM: Homo sapiens

<400> SEQUENCE: 60

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
            35                  40                  45

Met Ile Tyr Asp Val Ser Glu Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Tyr Val Phe Gly Thr Gly Thr Lys Leu Thr Val Leu
                100                 105                 110

<210> SEQ ID NO 61
<211> LENGTH: 115
<212> TYPE: PRT
<213> ORGANISM: Homo sapiens

<400> SEQUENCE: 61

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gln Asp Phe Asp Tyr Trp Gly Gln Gly Thr Leu Val Thr
                100                 105                 110

Val Ser Ser
        115

<210> SEQ ID NO 62
```

```
<211> LENGTH: 110
<212> TYPE: PRT
<213> ORGANISM: Homo sapiens

<400> SEQUENCE: 62

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln His Pro Asp Arg Ala Pro Lys Leu
        35                  40                  45

Met Leu Tyr His Val Thr Gln Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Ser Thr Tyr Val Phe Gly Thr Gly Thr Lys Val Thr Val Leu
                100                 105                 110
```